US007408359B2

United States Patent
Ide

(10) Patent No.: US 7,408,359 B2
(45) Date of Patent: Aug. 5, 2008

(54) CURRENT MEASURING DEVICE HAVING ARTIFICIAL LIPID BILAYER MEMBRANE

(75) Inventor: Toru Ide, Toyonaka (JP)

(73) Assignee: Japan Science and Technology Agency, Kawaguchi-shi, Saitama (JP)

( * ) Notice: Subject to any disclaimer, the term of this patent is extended or adjusted under 35 U.S.C. 154(b) by 1 day.

(21) Appl. No.: 10/572,569

(22) PCT Filed: Sep. 17, 2004

(86) PCT No.: PCT/JP2004/013671

§ 371 (c)(1),
(2), (4) Date: Mar. 17, 2006

(87) PCT Pub. No.: WO2005/029054

PCT Pub. Date: Mar. 31, 2005

(65) Prior Publication Data

US 2007/0035308 A1    Feb. 15, 2007

(30) Foreign Application Priority Data

Sep. 19, 2003    (JP)    ............................ 2003-328696

(51) Int. Cl.
G01N 27/02    (2006.01)
G01N 27/26    (2006.01)
(52) U.S. Cl. .................... 324/444; 324/439; 205/778
(58) Field of Classification Search ................ 324/444, 324/439; 205/778
See application file for complete search history.

(56) References Cited

U.S. PATENT DOCUMENTS 6,300,108 B1 *    10/2001    Rubinsky et al. ......... 435/173.6

7,201,836 B2 *    4/2007    Vogel et al. ............... 205/777.5

OTHER PUBLICATIONS

"Stochastic Sensors Inspired By Biology", H. Bayley & P.S. Cremer, Nature vol. 413, Sep. 13, 2001, 226-230, © 2001 Macmillian Magazines Ltd.

"Development of an Experimental Apparatus for Simultaneous Observation of Optical and Electrical Signals From Single Ion Channels", T. Ide, Y. Takeuchi and T. Yanagida, Single Molecules.3 (2002) 1, p. 33-42, © Wiley-VCH Verlag Berlin GmbH.

Toru Ide et al., "An Artificial Lipid Bilayer Formed On An Agarose-Coated Glass for Simultaneous Electrical And Optical Measurement of Single Ion Channels", Biochemical and Biophysical Research Communications vol. 265, No. 2, p. 595-599, © 1999.

(Continued)

Primary Examiner—Andrew H. Hirshfeld
Assistant Examiner—Amy He
(74) Attorney, Agent, or Firm—Harness, Dickey & Pierce, P.L.C.

(57) ABSTRACT

The current measuring device includes an upper solution chamber (3) and a lower solution chamber (8) whose bottom has a support layer (5) and measures a current flowing via an artificial lipid bilayer membrane (2) formed on a small hole (4) of the upper solution chamber (3), wherein the lower solution chamber (8) is provided below the upper solution chamber (3) by being surrounded with a bottom plate (6) and an interval keeping member (7a). An internal pressure of the lower solution chamber (8) is dropped so that the artificial lipid bilayer membrane (2) formed on the small hole (4) swells to the side of the lower solution chamber (8) so as to be thinner, and the thinner artificial lipid bilayer membrane (2) is supported by the support layer.

19 Claims, 15 Drawing Sheets

OTHER PUBLICATIONS

A. G. Macdonald et al., "Combined Spectroscopic And Electrical Recording Techniques In Membrane Research: Prospects of Single Channel Studies", Progress In Biophysics & Molecular Biology vol. 63, No. 1, p. 1-29, © 1995.

* cited by examiner (a)

(b)

(a)

(b)

(a)

(b)

CURRENT MEASURING DEVICE HAVING ARTIFICIAL LIPID BILAYER MEMBRANE

TECHNICAL FIELD

The present invention relates to a current measuring device having an artificial lipid bilayer membrane. Particularly, the present invention relates to a current measuring device which can not only measure a channel current of a single ion channel using an artificial lipid bilayer membrane but also optically observe the artificial lipid bilayer membrane.

BACKGROUND ART

An ion channel is a protein, penetrating a biological membrane, whose basic structure is a lipid bilayer membrane, and adjusts entrance and exit of ions according to stimulus so as to generate an electric signal or a calcium signal in a cell. That is, the ion channel is an important protein molecule for converting stimulus into an intracellular signal.

Such an ion channel is constituted of a pore serving as an ion path and a gate for controlling opening/closing of a channel. This opening/closing function can be confirmed by measuring an ion current at the time when the ion passes through the ion channel. As a method for measuring an ion current of a single ion channel, a patch-clamp method is adopted. Also a planar lipid bilayer method is adopted so as to measure the ion current.

In order to more deeply study correlation of structural functions of the ion channel, it is necessary to use a simple rearrangement system in carrying out an experiment. An artificial lipid bilayer membrane formation method adopted in this case is the planar lipid bilayer method. In the planar lipid bilayer method, a minimum simple system including ion, water, an artificial lipid bilayer membrane, and an ion channel is used so as to study a basic structure of the ion channel and detail correlation of structural functions thereof (Non-Patent Document 1 and the like).

The following specifically explains a system of the planar lipid bilayer method. As illustrated in FIG. 7, an ion channel 112 is provided in an artificial lipid bilayer membrane 111, and a current flowing via the ion channel 112 is measured. The artificial lipid bilayer membrane 111 is formed on a small hole 115 provided in a partition plate 114 such as a plastic plate for parting an aqueous solution chamber 113. In one of two chambers obtained by parting the aqueous solution chamber 113, an electrode 116 is provided. Via the electrode 116, a current measuring device 117 is provided. In the other chamber, an electrode 118 is provided. Via the electrode 118, an earth 119 causes the aqueous solution chamber 113 to be earthed.

Here, examples of how to form the artificial lipid bilayer membrane 111 on the small hole 115 include (A) vertical painting method, (B) vertical applying method, (C) horizontal formation method, and the like.

In the (A) vertical painting method, first, as illustrated in the left illustration of FIG. 8, with a thin glass tube or the like, lipid solution 110 is applied to the small hole 115 provided in a support such as the plate 114 for parting the aqueous solution chamber 113 (not shown in FIG. 8). Under this condition, the lipid solution 110 swells in directions of both surfaces of the partition plate 114 so as to cover the small hole 115. The lipid solution 110 is obtained by dissolving lipid in organic solvent such as decane. After applying the lipid solution 110, the lipid solution 110 moves on the surface of the plate 114 as illustrated in the right illustration of FIG. 8, thereby obtaining an artificial lipid bilayer membrane which has become thinner in a natural manner. Note that, the wording "become thinner" means a process in which the organic solvent or the like moves from a central portion of the applied lipid solution 110 so that a lipid bilayer membrane is formed in the central portion.

Next, in the (B) vertical applying method, as illustrated in the upper illustration of FIG. 9, a lipid monomolecular membrane 121 is developed on a gas-liquid interface of the aqueous solution chamber 113 (not shown in FIG. 9). At this time, a position of the gas-liquid interface is the same as a position of a lower side end of the small hole 115 provided in the partition plate 114. Thereafter, as illustrated in the middle illustration of FIG. 9, a liquid surface (gas-liquid interface) of one chamber (right side of the middle illustration) of two chambers obtained by parting the aqueous solution chamber 113 is raised, thereby developing the monomolecular membrane 121 on the surface of the partition plate 114. On this account, one opening side of the small hole 115 is covered by the monomolecular membrane 121. Thereafter, as illustrated in the lower illustration of FIG. 9, a liquid surface (gas-liquid interface) of the other chamber (left side of the lower illustration) of two chambers obtained by parting the aqueous solution chamber 113 is raised, thereby developing the monomolecular membranes 121 on the surface of the partition plate 114. On this account, also the other opening side of the small hole 115 is covered by the monomolecular membrane 121. As a result, on each opening side of the small hole 115, the monomolecular membrane 121 is applied, so that the artificial lipid bilayer membrane 111 is finally formed.

Next, in the (C) horizontal formation method, the aqueous solution chamber 113 illustrated in FIG. 13 is vertically parted with the partition plate 114. At this time, as illustrated in FIG. 10(a), the small hole 115 provided in the partition plate 114 is covered by the lipid solution 110, and the lipid solution 110 is left until the lipid solution 110 becomes thinner in a natural manner as the artificial lipid bilayer membrane 111. Alternatively, as illustrated in FIG. 10(b), a hydraulic pressure above the small hole 115 is raised in the chamber so that the lipid solution 110 swells downward so as to be thinner, thereby forming the artificial lipid bilayer membrane 111.

However, in any one of the artificial lipid bilayer membrane formation methods, it is difficult to quickly form a stable artificial lipid bilayer membrane 111. That is, in the (A) vertical painting method, it takes several minutes to dozens minutes for the lipid solution 110 to move on the surface of the partition plate 114 and become sufficiently thinner as the artificial lipid bilayer membrane 111. Further, in the (B) vertical applying method, it is essential to carry out a pre-treatment with respect to the small hole 115 with organic solvent such as squalene before forming the artificial lipid bilayer membrane 111, so that such a larger number of steps results in a more complicate formation method. Further, it is general that the artificial lipid bilayer membrane 111 is not formed unless the liquid surface is raised and lowered several times.

Further, in the (C) horizontal formation method, in case of leaving the lipid solution 110 covering the small hole 115 until the lipid solution 110 becomes thinner in a natural manner (in case of FIG. 10(a)), it is impossible to intentionally control the formation of the artificial lipid bilayer membrane. Therefore, it sometimes takes several hours for the lipid solution 110 to become thinner. Further, in case of raising the hydraulic pressure above the small hole 115 in the chamber so that the lipid solution 110 becomes thinner, the obtained artificial lipid bilayer membrane 111 has a thin portion serving as the "lipid bilayer membrane" and a thick portion referred to as a cyclic bulk phase surrounding the thin portion.

Thus, the artificial lipid bilayer membrane 111 obtained in this method is based on physicochemical balance of the foregoing portions. Thus, if these portions are physicochemically unbalanced by vibration caused by aqueous solution flow or the like, the artificial lipid bilayer membrane 111 is easily broken. Moreover, it is difficult to exactly control a pressure difference between the upper and lower chambers of the aqueous solution chamber 113, so that the obtained artificial lipid bilayer membrane 111 is likely to be unstable.

In case of adopting the planar lipid bilayer method, it is necessary to realize a great object: to form a stable and durable artificial lipid bilayer membrane.

Incidentally, it is considered that permeation of ions and structural change of ion channel molecules occur at the same time upon opening/closing a gate of the ion channel. In order to clarify a relationship between a structure and a function of the ion channel molecules, it is necessary to use a measuring device which can simultaneously measure the structure and the function of the ion channel molecules.

The inventors of the present invention proposed a current measuring device which improves the foregoing problems of the conventional artificial lipid bilayer membrane and can simultaneously measure the structure and the function of the ion channel molecules (for example, Non-Patent Document 2 and the like). As illustrated in FIG. 11, the current measuring device includes two solution chambers: an upper solution chamber 101 and a lower solution chamber 102. On a central portion of a bottom of the upper solution chamber 101, a film 103 having a small hole 105 is applied. Further, the lower solution chamber 102 has an opening 104 in its bottom, and a cover glass 106 is fixed on the opening 104 with an adhesive. On the cover glass 106, an agarose gel layer (not shown) is formed. Note that, as in the system of the planar lipid bilayer method, an electrode 116 is placed in the upper solution chamber 101, and a current measuring instrument 117 is provided via the electrode 116. In the lower solution chamber 102, an electrode 118 is placed, and an earth 119 causes the lower solution chamber 102 to be earthed via the electrode 1 18.

In the current measuring device, first, a lower portion of the upper solution chamber 101 is moved in the lipid solution so as to form a thick membrane made of lipid solution in the small hole 105. Thereafter, the upper solution chamber 101 is placed in the lower solution chamber 102, and the upper solution chamber 101 is lowered so that the thick membrane formed in the small hole 105 comes into contact with the agarose gel layer formed on the cover glass 106. Here, the pressure (hydraulic pressure) in the upper solution chamber 101 is raised so as to make a thick membrane thinner, thereby forming an artificial lipid bilayer membrane.

In the current measuring device, the pressure in the upper solution chamber 101 is raised, so that it takes less time to form an artificial lipid bilayer membrane (to make the thin membrane thinner). The thus formed artificial lipid bilayer membrane is supported by the agarose gel layer. Thus, even when a pressure is exerted by the upper solution chamber 101, the artificial lipid bilayer membrane is stabilized in upward and downward directions. Further, when the agarose gel layer is made thinner, it is possible to observe the artificial lipid bilayer membrane through a lens 107 whose numerical aperture (NA) is large. Thus, even in case where the ion channel is included in the artificial lipid bilayer membrane, the actual ion channel can be observed. On this account, it is possible to simultaneously measure a channel current and a structure of the ion channel.

Non-Patent Document 1
  Bayley, H., Cremer, P. Stochastic sensors inspired by biology, Nature 413, 226-230 (2001)

Non-Patent Document 2
  Ide, T., Takeuchi, U., Yanagida, T. Development of an Experimental Apparatus for Simultaneous Observation of Optical and Electrical Signals from Single Ion Channels, Single Mol. 3(2002)1, pages 33-42

However, the conventional current measuring device is insufficient in terms of the stability and the size reduction of the artificial lipid bilayer membrane, so that a current measuring device having higher performance is required.

Specifically, first, the conventional current measuring device is arranged so that: as illustrated in FIG. 12, the artificial lipid bilayer membrane 111 formed on the small hole 105 provided in the film 103 is supported by the agarose gel layer on the cover glass 103, so that the artificial lipid bilayer membrane 111 is stabilized in upward and downward directions. However, both the upper solution chamber 101 and the lower solution chamber 102 are open, a higher pressure in the upper solution chamber 101 causes vibration of aqueous solution flow to destabilize the artificial lipid bilayer membrane 111 in a direction (H direction in FIG. 12) parallel to a bottom of the upper solution chamber 101 (not shown in FIG. 12).

Thus, in the conventional current measuring device, it is impossible to strictly keep a curvature of the artificial lipid bilayer membrane 111. Thus, in the aforementioned (C) horizontal formation method, as in the case of raising the hydraulic pressure above the small hole 115 in the chamber so as to make the membrane thinner (FIG. 10(*b*)), the artificial lipid bilayer membrane 111 and the cyclic bulk phase are physicochemically unbalanced, so that the artificial lipid bilayer membrane 111 is broken.

Further, in the conventional current measuring device, two solution chambers are used, so that it is difficult to reduce the size of the current measuring device. Thus, it is actually impossible to produce the artificial lipid bilayer membrane on the small-size chip.

DISCLOSURE OF INVENTION

The present invention was made in view of the foregoing problems, and an object of the present invention is to provide a current measuring device, capable of quickly forming a stable artificial lipid bilayer membrane, whose size can be reduced, the current measuring device having the artificial lipid bilayer membrane and being favorably applicable to simultaneous measurement of a structure and a function of a single channel for example.

A current measuring device according to the present invention, which is capable of measuring a current flowing via an artificial lipid bilayer membrane, includes: an upper solution chamber which is capable of containing aqueous solution; and a lower solution chamber disposed below the upper solution chamber, a bottom of the upper solution chamber having a membrane formation opening, a bottom of the lower solution chamber having a support layer for supporting the artificial lipid bilayer membrane, the artificial lipid bilayer membrane formed on the membrane formation opening of the upper solution chamber being brought into contact with the support layer so as to be supported, and the current measuring device further includes: a bottom plate on which the support layer is placed; and an interval keeping member for keeping a predetermined interval between the upper solution chamber and the bottom plate, wherein the lower solution chamber is provided below the upper solution chamber by being surrounded with the bottom plate and the interval keeping member, and the artificial lipid bilayer membrane formed on the membrane formation opening is swollen to a side of the lower solution chamber so as to be made thinner and come into contact with the support layer so that the artificial lipid bilayer membrane is supported on the support layer.

According to the foregoing arrangement, the lower solution chamber is not open, vibration caused by the aqueous solution flow is suppressed, so that it is possible to form an artificial lipid bilayer membrane which is stable also in a direction parallel to the bottom of the upper solution chamber.

For a fuller understanding of the nature and advantages of the invention, reference should be made to the ensuing detailed description taken in conjunction with the accompanying drawings.

BRIEF DESCRIPTION OF DRAWINGS

In FIG. 2, (b) is a partial cross sectional view illustrating a state in which an artificial lipid bilayer membrane is in contact with a support layer so as to be thinner.

In FIG. 6, (b) is a partial cross sectional view illustrating a state in which the artificial lipid bilayer membrane is in contact with the support layer so as to be thinner.

FIG. 10 (b) shows a horizontal formation method using hydraulic pressure.

FIG. 14 (b) illustrates a trace of the current in case where the aqueous solution includes 100 mM KCl and 1 mM $CaCl_2$.

In FIG. 16, (b) illustrates a current trace measured in Example 2.

In FIG. 17, (b) illustrates a fluorescent image of a ryanodine receptor channel measured or observed in Example 3. In FIG. 17, (c) illustrates a fluorescent image of ryanodine measured or observed in Example 3. In FIG. 17, (d) illustrates a current trace measured or observed after addition of ryanodine in Example 3. In FIG. 17, (e) illustrates a fluorescent image of a ryanodine receptor channel measured or observed in Example 3. In FIG. 17, (f) illustrates a fluorescent image of ryanodine measured or observed in Example 3.

BEST MODE FOR CARRYING OUT THE INVENTION

Embodiment 1

Figure 1:
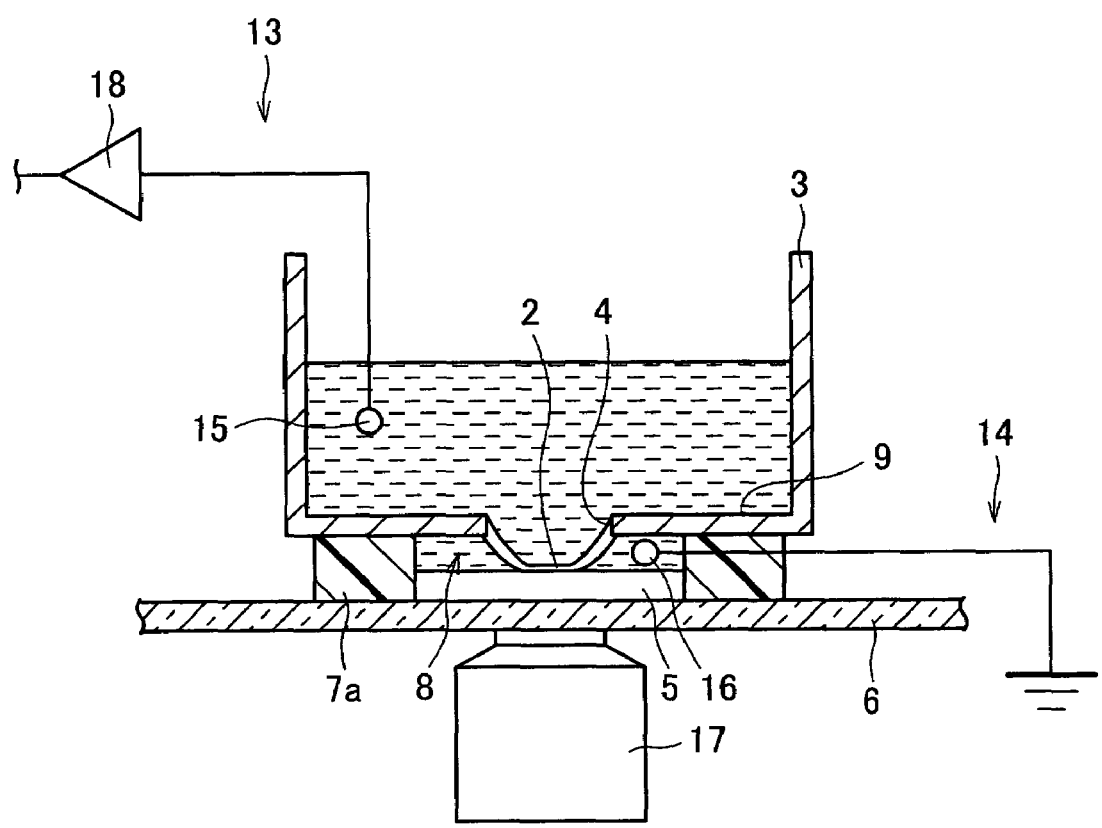
FIG. 1 is a cross sectional view schematically illustrating a structure of a current measuring device according to the present invention.
Figure 2:
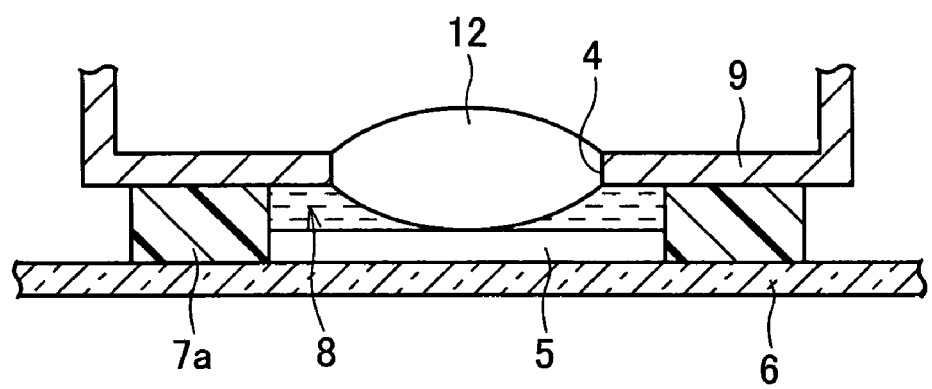
In FIG. 2, (a) is a partial cross sectional view illustrating a state in which lipid solution is applied to a small hole of an upper solution chamber in the current measuring device of FIG. 1.
Figure 2:
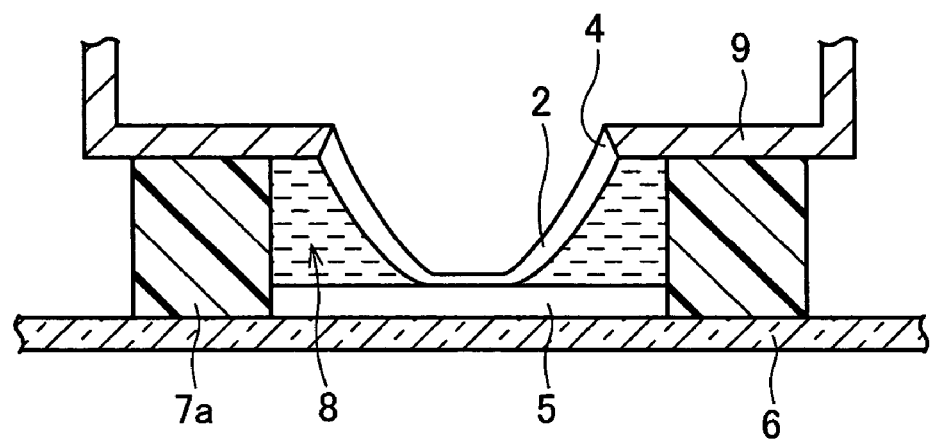
Figure 3:
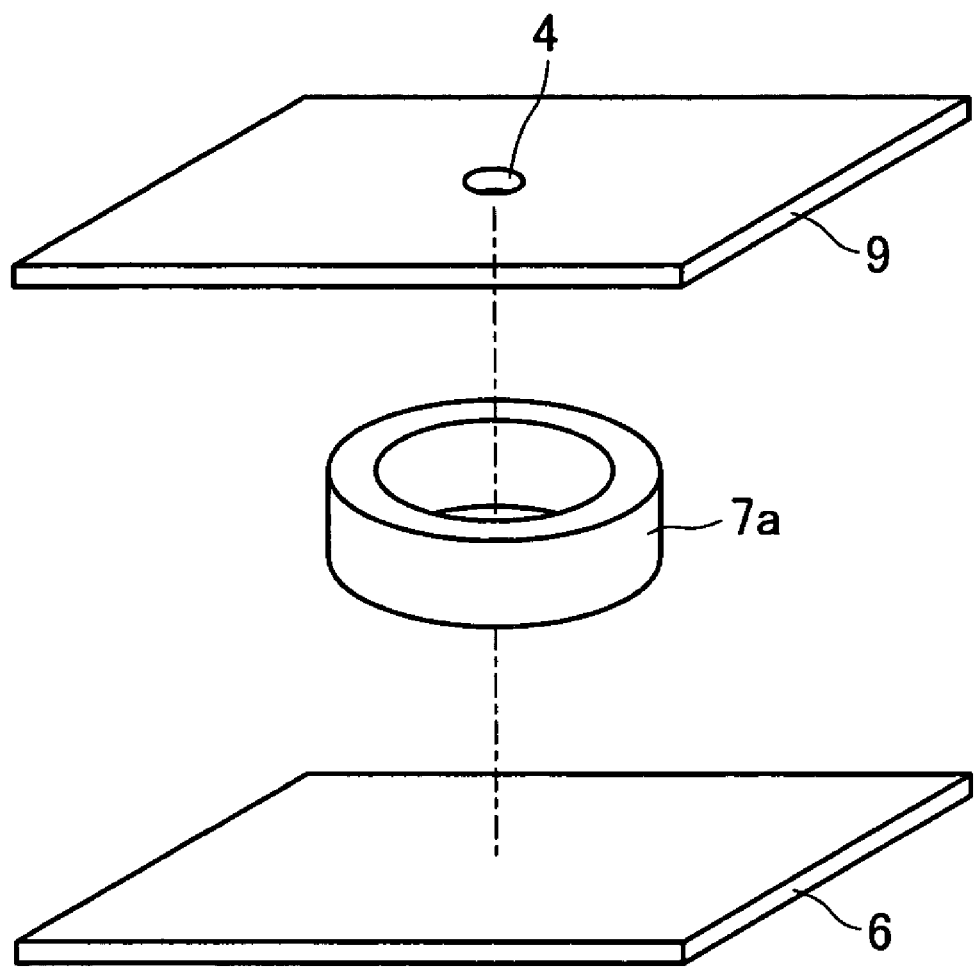
FIG. 3 partially illustrates how members constituting a lower solution chamber are assembled.

The following explains one embodiment of the present invention with reference to FIG. 1 to FIG. 3. Note that, it is needless to say that the present invention is not limited only to recitations of the present embodiment.

(1) An Example of a Current Measuring Device Having an Artificial Lipid Bilayer Membrane FIG. 1 is a cross sectional view schematically illustrating a current measuring device according to the present invention. In FIG. 2, (a) and (b) are cross sectional views each of which illustrates a state in which an artificial lipid bilayer membrane is formed. FIG. 3 illustrates how members constituting the current measuring device of FIG. 1 are assembled. Note that, FIG. 3 illustrates not an entire view but only a bottom of an upper solution chamber.

As illustrated in FIG. 1, a current measuring device 1 according to the present invention includes an artificial lipid bilayer membrane 2, an upper solution chamber 3, a support layer 5, a bottom plate 6, an interval keeping member 7a, a current measuring section 13, and an earthing section 14. The artificial lipid bilayer membrane 2 is formed on a small hole (membrane formation opening) 4 provided in a bottom 9 of the upper solution chamber 3. A lower solution chamber 8 is formed below the upper solution chamber 3 so as to be surrounded by the bottom plate 6 and the interval keeping member 7a. Further, in the current measuring device 1, the artificial lipid bilayer membrane 2 formed on the small hole 4 of the upper solution chamber 3 is swollen to the side of the lower solution chamber 8 so that the artificial lipid bilayer membrane 2 is in contact with the support layer with the membrane being thinner so as to be supported on the support layer 5. Note that, it is preferable that an optical microscope (optical observation means) 17 is provided below the bottom plate 6.

According to the foregoing arrangement, the lower solution chamber 8 is not open, so that vibration caused by the aqueous solution flow is suppressed, so that the artificial lipid bilayer membrane 2 formed on the small hole 4 can be stabilized also in a direction parallel to the bottom of the upper solution chamber 3.

<Artificial Lipid Bilayer Membrane>

As described above, the artificial lipid bilayer membrane 2 is formed on the small hole 4 provided in the bottom 9 of the upper solution chamber 3. As will be described later, the artificial lipid bilayer membrane 2 is formed as follows: after applying lipid solution to the small hole 4, an internal pressure of the lower solution chamber 3 is dropped so that the aqueous solution in the upper solution chamber 3 is made to flow via an upper portion of the artificial lipid bilayer membrane 2 into the lower solution chamber 8 so as to cause the artificial lipid bilayer membrane 2 to swell downward, thereby bringing the artificial lipid bilayer membrane 2 into contact with the support layer 5.

The artificial lipid bilayer membrane 2 is similar to a biological membrane including an ion channel in which opening/closing of its gate allows an ion to pass therethrough. By using a single lipid mixture or a lipid mixture having a desired composition, it is possible to provide a simplified model channel. Note that, the ion channel will be detailed later.

The lipid is not particularly limited as long as the lipid constitutes the artificial lipid bilayer membrane 2, but phospholipid is favorably used. Specific examples thereof include phosphatidylcholine, diphytanoil phosphatidylcholine, phosphatidylethanolamine, phosphatidylcerine, and the like.

Two hydrocarbon chains of the phospholipid may be saturated hydrocarbon or may be unsaturated hydrocarbon. As the lipid, pure lipid may be used or a mixture of two or more kinds of the lipids may be used. In order to keep the activity of the ion channel, cholesterol or the like may be added as required for example.

The lipid solution is a solution obtained by dispersing the lipid in organic solvent. The organic solvent used is not particularly limited as long as the organic solvent is nonpolar organic solvent. As a specific example thereof, saturated hydrocarbon such as decane, hexadecane, and hexane is favorably used. Further, the lipid concentration preferably ranges from 5 to 40 mg/mL, more preferably from 15 to 20 mg/mL.

<Upper Solution Chamber>

An arrangement of the upper solution chamber 3 is not particularly limited as long as the small hole 4 is provided in the bottom 9 and the upper solution chamber 3 can contain aqueous solution. As long as the upper solution chamber 3 is arranged in this manner, it is possible to form the artificial lipid bilayer membrane 2 on the small hole 4 as will be described later.

Any arrangement is possible as long as the small hole 4 is formed in the bottom 9 of the upper solution chamber 3, but it is more preferable to form the artificial lipid bilayer membrane 2 on a central portion of the bottom. On this account, it is possible to easily carry out optical observation from underneath. Further, it may be so arranged that the small hole 4 is formed directly on the bottom 9, or it may be so arranged that an opening is provided in the bottom 9 of the upper solution chamber 3 and a film having the small hole 4 is combined to the opening. A diameter of the small hole 4 is preferably 10 μm or more and 500 μm or less, more preferably 50 μm or more and 200 μm or less. On this account, it is possible to favorably form the artificial lipid bilayer membrane.

A material of the bottom 9 or the film having the small hole 4 is not particularly limited, but specific favorable examples thereof include: plastic such as polypropylene, polyvinylchloride, and polystyrene; fluorine resin such as polytetrafluoroethylene; and the like. Further, it is preferable that the thickness of the bottom 9 or the film having the small hole 4 is 0.1 mm or more and 0.3 mm or less. Further, it is preferable that only a portion around the small hole 4 in the bottom 9 or the film is made thinner than other portion of the bottom 9 or the film. On this account, it is possible to quickly form a stable artificial lipid bilayer membrane.

The small hole 4 can be formed by the following conventional known method for example. First, a stainless rod which has been pointed into a sharp cone is heated with a gas burner or the like. Subsequently, the heated stainless rod is firmly pressed against a surface in which the small hole 4 is to be formed. The pressing of the stainless rod is continued until a back surface of the pressed surface slightly swells. This slightly swelling portion is cut with a razor, thereby providing the small hole 4. Note that, the small hole 4 is rinsed with chloroform/methanol so that impurities and the like are removed. Of course, a method for providing the small hole 4 is not limited to this, and any known method can be applied.

A shape of the upper solution chamber 3 is not particularly limited, but an example thereof is a cylindrical shape. Further, a size of the upper solution chamber 3 is particularly limited. However, in case where the upper solution chamber 3 has a cylindrical shape for example, its internal diameter is preferably 0.5 mm or more and 20 mm or less, more preferably 1.0 mm or more and 10 mm or less. Further, the size of the upper solution chamber 3 can be reduced so that the internal diameter is 0.5 mm, more preferably 10 μm. Further, a volume of the upper solution chamber 3 is not particularly limited, but it is preferable that the volume is 0.01 $cm^3$ or more and 1.0 $cm^3$ or less. Further, it is possible to reduce the volume of the upper solution chamber 3 to 0.001 $cm^3$. On this account, it is possible to provide the artificial lipid bilayer membrane formation device according to the present invention on a small-size chip, so that it is possible to manufacture a smaller sensor.

Further, in the upper solution chamber 3, a material of a portion other than the portion in which the small hole 3 is provided is not particularly limited, but examples thereof include glass, plastic, and the like.

The upper solution chamber 3 can contain the aqueous solution. Each side of the artificial lipid bilayer membrane formed on the small hole 4 is in contact with the aqueous solution with which the upper solution chamber 3 and the lower solution chamber are filled. This condition is not different in a case where the artificial lipid bilayer membrane's portion positioned on the side of the lower solution chamber 8 is in contact with the support layer 5 described later. That is, the artificial lipid bilayer membrane is in contact with the aqueous solution penetrating the support layer 5. The aqueous solution is not particularly limited as long as the aqueous solution does not include surfactant, organic solvent, and the like. A favorable example of the aqueous solution is aqueous solution of potassium chloride, sodium chloride, calcium chloride, or the like.

Further, it is preferable that the upper solution chamber 3 can be moved in upward and downward directions. The upper solution chamber 3 may be moved in upward and downward directions manually or by using a moving instrument. A specific example of the moving instrument is a micro manipulator or the like.

<Lower Solution Chamber>

The lower solution chamber 8 may be arranged in any manner as long as: the lower solution chamber 8 is disposed under the upper solution chamber 3 and is surrounded by the bottom plate 6 and the interval keeping member 7a. On a bottom of the lower solution chamber 8, that is, on a surface of the bottom plate 6, the support layer 5 for supporting the artificial lipid bilayer membrane 2 is provided. Further, the artificial lipid bilayer membrane 2 formed on the small hole 4 in the upper solution chamber 3 is brought into contact with the support layer 5 so as to be supported.

The lower solution chamber 8 is provided to form the artificial lipid bilayer membrane 2 on the small hole 4 in the bottom 9 of the upper solution chamber 3 and to stably support the formed artificial lipid bilayer membrane 2 with the support layer 5. In this view point, in the current measuring device 1 according to the present invention, an arrangement of the lower solution chamber 8 is not specifically limited, but it is preferable that the lower solution chamber 8 is surrounded by the bottom plate 6 and the interval keeping member 7a as described in the present embodiment.

A volume of the lower solution chamber 8 is not particularly limited, but the volume is preferably 0.1 mm$^3$ or more and 10 mm$^3$ or less, more preferably 0.5 mm$^3$ or more and 3.5 mm$^3$ or less. On this account, it is possible to provide the artificial lipid bilayer membrane formation device according to the present invention on a small-size chip, so that it is possible to manufacture a smaller sensor.

Next, the bottom plate 6 and the interval keeping member 7a which constitute the lower solution chamber 8 are described as follows.

<Bottom Plate>

The bottom plate 6 is provided below the upper solution chamber 3 so as to be substantially parallel to a bottom of the upper solution chamber 3, and the interval keeping member 7a is disposed between the bottom plate 6 and the upper solution chamber 3. Below the upper solution chamber 3, the lower solution chamber 8 is provided with it surrounded by the bottom plate 6 and the interval keeping member 7a. An arrangement of the bottom plate 6 is not particularly limited, and any arrangement is possible as long as the support layer 5 can be placed on the surface. Thus, a shape, a size, a surface condition, and the like of the bottom plate 6 are not particularly limited, and a suitable shape, a suitable size, a suitable surface condition, and the like may be set according to the current measuring device 1 finally obtained or the support layer formed.

A material and the like of the bottom plate 6 are not particularly limited. However, in case of carrying out optical observation from underneath, i.e., from the backside of the bottom plate 6's surface contacting the upper solution chamber 3 for example, it is preferable to use a translucent material. Specific examples thereof include: glass; plastic such as polystylene; and the like. This allows observation from underneath with the optical microscope 17.

Further, the thickness of the bottom plate 6 is not particularly limited, but it is preferable that the thickness is 0.1 mm or more and 1.0 mm or less. On this account, it is possible to obtain favorable mechanical strength. Further, in case of carrying out the optical observation from underneath for example, the thickness of the bottom plate 6 is not particularly limited as long as the thickness is suitably set according to optical observation conditions (for example, a working distance and the like of the objective lens), but it is more preferable that the thickness is 0.1 mm or more and 0.17 mm or less. On this account, it is possible to favorably carry out the optical observation using an objective lens whose numerical aperture is high.

Further, as described above, the support layer 5 for supporting the artificial lipid bilayer membrane 2 is formed on the bottom plate 6's surface contacting the upper solution chamber 3, that is, on the bottom of the lower solution chamber 8.

The support layer 5 is not particularly limited as long as the support layer 5 allows permeation of the aqueous solution and can support the artificial lipid bilayer membrane 2. A specific example of the support layer 5 is a porous membrane such as a polymer gel membrane, a cellulose membrane, and the like. Among them, it is more preferable that the support layer 5 is made of polymer gel. The polymer gel is not particularly limited, but a polysaccharide such as agarose and a hydrophilic resin such as polyacrylamide can be favorably used. By using these materials, it is possible to easily form the support layer 5 with inexpensive and highly reliable materials.

The thickness of the support layer 5 is not particularly limited, but the thickness is preferably 50 nm or more and 2 mm or less, more preferably 100 nm or more and 1 mm or less. On this account, it is possible to produce a current measuring device having a favorable size. Further, in case of carrying out the optical observation for example, the thickness of the support layer 5 is not particularly limited as long as its working distance is shorter than a working distance of the objective lens. However, the thickness is more preferably 50 nm or more and 20 μm or less, still more preferably 100 nm or more and 20 μm or less. On this account, it is possible to favorably carry out the optical observation using an objective lens whose numerical aperture is high. That is, in the optical observation using the objective lens whose numerical aperture is high, it is preferable to reduce a distance between the artificial lipid bilayer membrane and the objective lens. For example, in case of using an objective lens whose numerical aperture is about 1.4 in carrying out fluorescent observation with respect to an ion channel single molecule, it is preferable to position the artificial lipid bilayer membrane 2 above the surface of the bottom plate 6 by not more than 20 μm so that the surface is opposite to the side of the support layer 5. On this account, it is possible to effectively operate the objective lens. Further, in case of using near field light for example, it is preferable that the thickness of the support layer 5 is 100 nm or more and 200 nm or less. On this account, it is possible to favorably observe a fluorescent substance in the solution. In case of using the near field light, it is preferable to position the artificial lipid bilayer membrane 2 above the surface of the bottom plate 6 by 100 nm or more and 200 nm or less so that the surface is opposite to the side of the support layer 5. On this account, it is possible to favorably carry out the optical observation using the near field light.

Further, a method for forming the support layer 5 is not particularly limited, and a conventional known method may be adopted. A specific example thereof is as follows: in case of using agarose (polymer gel), agarose dispersion liquid is prepared, and the thus prepared liquid is heated so that agarose is dissolved, and then the liquid is applied to the bottom plate 6, and the applied liquid is dried at a room temperature.

The artificial lipid bilayer membrane 2 formed on the small hole 4 of the upper solution chamber 3 is swollen to the side of the lower solution chamber 8 so that the artificial lipid bilayer membrane 2 is in contact with the support layer with the membrane being thinner so as to be supported on the support layer 5. On this account, even when a pressure in the upper solution chamber 3 and a pressure in a lower solution chamber are different from each other, the artificial lipid bilayer membrane 2 is supported by the support layer 5 so as to be stable in upward and downward directions.

<Interval Keeping Member>

As illustrated in FIG. 1 to FIG. 3, the interval keeping member 7a is disposed between the upper solution chamber 3 and the bottom plate 6 and keeps a predetermined interval between the upper solution chamber 3 and the bottom plate 6. Further, the bottom plate 6 and the interval keeping member 7a surround so that the lower solution chamber 8 is provided below the upper solution chamber 3 as described above.

Figure 12:
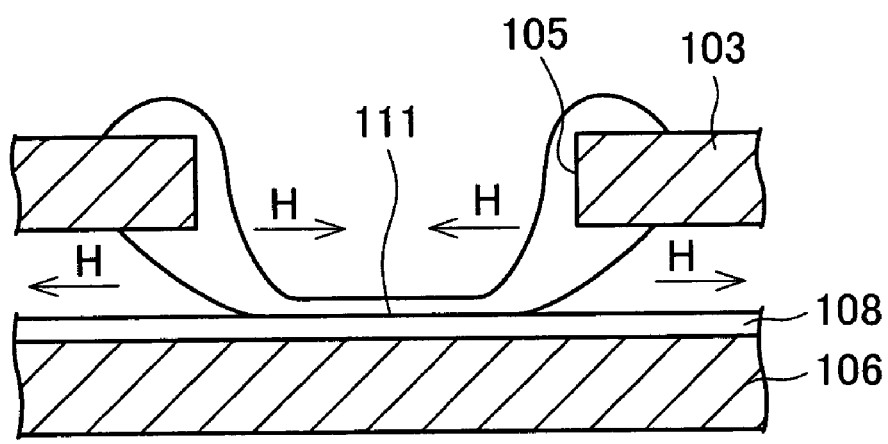
FIG. 12 illustrates an artificial lipid bilayer membrane formed on a conventional polymer gel layer.

The interval keeping member 7a is not particularly limited as long as the interval keeping member 7a keeps a predetermined interval between the upper solution chamber 3 and the bottom plate 6 and has a shape which allows formation of the lower solution chamber 8. In the present embodiment, for example, the interval keeping member 7a is arranged so that: the interval keeping member 7a internally has a hollow portion, and the hollow portion can contain the aqueous solution with which the lower solution chamber 8 is to be filled. Further, the lower solution chamber 8 is tightly closed by the interval keeping member 7a, the upper solution chamber 3, the bottom plate 6, and the artificial lipid bilayer membrane 2. In this manner, the lower solution chamber 8 is closed, so that it is possible to form the artificial lipid bilayer membrane 2 which is stable in a direction parallel to the bottom plate 6 even when a pressure in the upper solution chamber 3 and a pressure in a lower solution chamber are different from each other. This is because the tightly closed lower solution chamber 8 does not allow the aqueous solution flow caused in case where the upper and lower solution chambers are open (see FIG. 12).

Both upper and lower portions of the interval keeping member 7a used in the present embodiment are open, and the interval keeping member 7a has a cylindrical shape or a prismatic shape which internally has a hollow portion. The interval kept by the interval keeping member 7a, that is, the height of the cylindrical shape or the prismatic shape is set so that the artificial lipid bilayer membrane 2 formed on the small hole 9 of the upper solution chamber 3 swells to the side of the lower solution chamber and comes into contact with the support layer 5 formed on the bottom plate 6. Further, as illustrated in FIG. 3, it is more preferable that the interval keeping member 7a has the cylindrical shape, and a diameter of the cylindrical shape is preferably 0.25 mm or more and 2.5 mm or less, more preferably 0.5 mm or more and 1.5 mm or less. On this account, it is possible to set the volume of the lower solution chamber 8 within the aforementioned range. Further, in case where the interval keeping member 7a has the cylindrical shape, a difference between its internal diameter and external diameter, that is, the thickness of a side face of the lower solution chamber 8 is preferably 0.05 mm or more and 0.5 mm or less, more preferably 0.1 mm or more and 0.3 mm or less. On this account, it is possible to more tightly close the lower solution chamber 17.

The interval keeping member 7a used in the present embodiment can change the interval between the upper solution chamber 3 and the bottom plate 6, and the change in the interval allows the artificial lipid bilayer membrane 2 formed on the small hole 4 of the upper solution chamber 3 to swell to the side of the lower solution chamber 8.

Specifically, as illustrated in FIG. 2(a), the lipid solution 12 is applied to the small hole 4 of the upper solution chamber 3 under such condition that the interval kept by the interval keeping member 7a is reduced. Thereafter, as illustrated in FIG. 2(b), when the interval is increased, the aqueous solution in the upper solution chamber 3 flows via an upper portion of the artificial lipid bilayer membrane 2 to the side of the lower solution chamber 8, and a lower portion of the artificial lipid bilayer membrane 2 swells downwardly so as to be in contact with the support layer 5. Under this condition, the artificial lipid bilayer membrane 2 is supported by the support layer 5. In this manner, the interval kept by the interval keeping member 7a is changed, thereby quickly forming the artificial lipid bilayer membrane 2.

Thus, the interval keeping member 7a for changing the interval is not particularly limited as long as it is possible to change the interval kept by the interval keeping member 7a. The interval keeping member 7a may be arranged so as to mechanically change the interval or may be arranged so as to change the interval due to a property of a material constituting the interval keeping member 7a. A favorable example thereof is the following arrangement: the interval keeping member 7a is made of elastic material which allows the interval keeping member 7a to expand and contract. For example, various kinds of elastomer can be used as the elastic material. Among them, it is more preferable to use silicone rubber in view of the durability and the safety.

Further, as illustrated in FIG. 3, the method in which the interval keeping member 7a and the bottom plate 6 are used to form the lower solution chamber 8 so that the lower solution chamber 8 is tightly closed by the bottom 9 of the upper solution chamber 3 is not particularly limited. Examples thereof are: a method in which the three members are brought into tightly contact with each other so as to be cramped with screws; and a method in which the three members are pressed and fixed with fixing means such as a clip.

<Current Measuring Section/Earthing Section>

The current measuring section (current measuring means) 13 is not particularly limited as long as the current measuring section 13 is electrically connected to the upper solution chamber 3 and can measure a current flowing via an ion channel provided in the artificial lipid bilayer membrane 2.

As illustrated in FIG. 1, the current measuring section 13 is specifically arranged so as to include: an electrode 15 placed in the upper solution chamber 3; an amplifier 18 connected to the electrode 15; and an ampere meter (not shown) electrically connected to the amplifier 18. An example of the electrode 15 is an Ag—AgCl electrode or the like, but the electrode 15 is not limited to this. Neither the amplifier 18 nor the ampere meter are particularly limited, and known devices can be used as the amplifier 18 and the ampere meter.

In case of electrically connecting the current measuring section 13 to the upper solution chamber 13, the lower solution chamber 8 is essentially earthed. The earthing section (earthing means) 14 used at this time is not particularly limited as long as the earthing section 14 is electrically connected to the lower solution chamber 8. For example, as illustrated in FIG. 1, the earthing section 14 is arranged so that an electrode 16 is placed in the lower solution chamber 8 so as to earth the lower solution chamber 8 via the electrode 16. Note that, the same kind of electrode as the electrode 15 can be used as the electrode 16.

Further, also a specific method for causing the current measuring section 13 to measure a current is not particularly limited. However, examples thereof include: a patch-clamp method; a method in which an ion channel is provided in the artificial lipid bilayer membrane so as to measure a current flowing therethrough; and the like. On this account, it is possible to observe a function of the ion channel, and it is possible to identify an assay and to determine the quantity of the assay in accordance with (i) a shape indicative of how the current changes, (ii) how much the current changes, and (iii) how often the current changes.

<Optical Microscope>

In the current measuring device according to the present invention, it is preferable to provide the optical microscope (optical observation means) 17 below the bottom plate 6, that is, on the bottom plate 6 so that the optical microscope 17 is positioned on the backside of the side having the support layer 5. On this account, it is possible to measure a current flowing via the ion channel and to optically observe the ion channel at the same time. Of course, in the present invention, means other than the optical microscope 17 can be favorably used as long as it is possible to optically observe the ion channel through the means (optical observation means). Specifically, it is possible to use a near field light excitation fluorescent microscope and the like for example, but the optical observation means is not particularly limited.

Examples of the observation carried out through the optical microscope 17 include: observation of how the fluorescent intensity of the fluorescent-labeled ion channel changes with closing/opening of the gate; observation of how the ion channel moves; observation of how the spectrum changes due to energy transfer between two fluorescent dyes; and the like. Further, it is possible to confirm the formation of the artificial lipid bilayer membrane 2 with the optical microscope 17. Furthermore, it is possible to observe movement of the lipid molecules by using the artificial lipid bilayer membrane 2 including the fluorescent-labeled lipid. Of course, the optical measurement is not limited to them, and various conventional known methods are adoptable.

<Ion Channel>

By providing the ion channel in the artificial lipid bilayer membrane 2, the current measuring device according to the present invention can be favorably used to simultaneously measure a structure and a function of the ion channel. That is, the artificial lipid bilayer membrane 2 including the ion channel therein is used to measure a current flowing via the ion channel, thereby observing a condition under which a physiologically active substance or an analyte coupled with the ion channel as stimulus inhibits or activates a current, or measuring concentration of the physiologically active substance or the analyte.

The ion channel provided in the artificial lipid bilayer membrane 2 may be separated/purified from a biological membrane, or may be prepared by using a biogenetical technique, or may be artificially synthesized. Thus, the ion channel is not particularly limited. Specific examples thereof include an $Na^+$ channel, a $K^+$ channel, a $Ca^{2+}$ channel, an alamethicin channel, a ryanodine receptor channel, a hemolysin channel, and the like.

As a method for providing the ion channel in the artificial lipid bilayer membrane, a conventional known method can be adopted, and the method is not particularly limited. A specific example thereof is a method in which: a membrane fraction including an ion channel is made soluble with surfactant, and the membrane fraction is rearranged into a membrane vesicle, and the membrane vesicle is fused with the artificial lipid bilayer membrane.

(2) How to Form the Artificial Lipid Bilayer Membrane

Next, as to the current measuring device according to the present invention, the following explains how to form the artificial lipid bilayer membrane 2 on the small hole 4 provided in the bottom of the upper solution chamber 3 with reference to FIG. 2.

Specifically, in the present embodiment, the interval keeping member 7a can change the interval between the upper solution chamber 3 and the bottom plate 6. Thus, the following explains a case where an elastic material is adopted as the interval keeping member 7a, and explains how to quickly form the artificial lipid bilayer membrane 2 by changing the interval due to the upward and downward expansion and contraction of the elastic material.

First, the upper solution chamber 3 and the lower solution chamber 8 are filled with the aqueous solution. Next, as illustrated in FIG. 2(a), the lipid solution 12 is applied to the small hole 4 with the interval keeping member 7a contracted. Thereafter, as illustrated in FIG. 2(b), the upper solution chamber 3 is gradually raised, so that the aqueous solution in the upper solution chamber 3 via the upper portion of the artificial lipid bilayer membrane 2 into the lower solution chamber 8. As a result, the artificial lipid bilayer membrane 2 swells downwardly. In this manner, the artificial lipid bilayer membrane 2 comes into contact with the support layer 5 so as to be thinner.

The interval keeping member 7a is expanded and contracted so as to change the interval in this manner, thereby forming the artificial lipid bilayer membrane 2 in several seconds. Further, it is possible to form the artificial lipid bilayer membrane 2 more stably than the conventional case where a pressure in the upper solution chamber 3 is raised so as to swell the artificial lipid bilayer membrane 2 to the side of the lower solution chamber. In the method in which the pressure in the upper solution chamber 3 is raised, a curvature of the artificial lipid bilayer membrane 2 is not constant particularly in the open chamber. In addition, the lipid existing in the cyclic bulk phase and in the bottom 9 so as to be positioned around the small hole 4 successive to the cyclic bulk phase is laterally dispersed, and the artificial lipid bilayer membrane 2 excessively swells in a lateral direction, so that the curvature increases with time. This results in instability of the artificial lipid bilayer membrane 2. In contract, according to the method in which the interval keeping member 7a is expanded and contracted, the pressure in the lower solution chamber 8 is dropped, so that the instability caused by the lateral dispersion of the lipid does not occur.

Further, according to the method in which the pressure in the upper solution chamber 3 is raised, in case of controlling the curvature particularly in the open chamber, it is necessary to exert an extraordinarily high pressure in determining the curvature of the artificial lipid bilayer membrane 2 whose area size is small. That is, the upper solution chamber has to contain larger quantity of aqueous solution in order to raise the hydraulic pressure in the upper solution chamber. For example, it is necessary that the depth of the aqueous solution ranges is about 3 to 5 mm in order to determine the curvature of the artificial lipid bilayer membrane whose diameter is 500 μm, but it is necessary that the depth of the aqueous solution is 20 mm or more in order to determine the curvature of the artificial lipid bilayer membrane whose diameter is 50 μm. This raises such problem that a larger device is required in forming an artificial lipid bilayer membrane 2 whose area size is smaller. In contract, in case of dropping the pressure in the lower solution chamber 8, this technique is free from the foregoing problem, so that it is possible to form the artificial lipid bilayer membrane 2 whose area size is small without increasing the size of the upper solution chamber 3. Further, it is possible to reduce the size of the artificial lipid bilayer membrane 2, so that it is possible to reduce the electric noise.

Further, the upper solution chamber 3 is open, and the lower solution chamber 8 is tightly closed by the artificial lipid bilayer membrane 2, the bottom 9 of the upper solution chamber 3, the interval keeping member 7a, and the bottom plate 6. Thus, the artificial lipid bilayer membrane 2 is stabilized in a direction parallel to the bottom plate 6 which was conventionally instable, so that it is possible to further improve the durability of the artificial lipid bilayer membrane 2.

Thus, the present invention includes also the method for forming the artificial lipid bilayer membrane 2 in the foregoing manner. Specifically, in the artificial lipid bilayer membrane formation method according to the present invention, the upper solution chamber whose bottom 9 has a membrane formation opening (small hole 4) and the lower solution chamber 8 are used. The lower solution chamber 8 is disposed below the upper solution chamber 3, and includes (i) the bottom plate 6 placed on the surface of the support layer 5 for supporting the artificial lipid bilayer membrane 2 and (ii) the interval keeping member 7a for keeping a predetermined interval between the upper solution chamber 3 and the bottom plate 6, and the lower solution chamber 8 is provided with it surrounded by the bottom plate 6 and the interval keeping member 7a. Here, the interval keeping member 7a can change the interval between the upper solution chamber 3 and the bottom plate 6. The artificial lipid bilayer membrane formation method according to the present invention includes the steps of: (i) applying the lipid solution 12 to the membrane formation opening (small hole 4) under such condition that surfaces of the membrane formation opening (small hole 4) which are respectively positioned on the side of the upper solution chamber 3 and the side of the lower solution chamber 8 are in contact with the aqueous solution and under such condition that the interval is kept small; and (ii) increasing the interval so that the artificial lipid bilayer membrane 2 is in contact with the support layer 5 so as to make the artificial lipid bilayer membrane thinner.

(3) Use of the Present Invention

In the current measuring device according to the present invention, it is possible to further stabilize the formed artificial lipid bilayer membrane 2, so that it is possible to simultaneously measure a structure and a function of an ion channel in a sufficiently stable manner even in case where the ion channel is provided in the artificial lipid bilayer membrane 2.

A specific example of use of the current measuring device according to the present invention is as follows: for example, the current measuring device can be used in screening a drug made by using ion channel proteins concerning a certain disease.

There are many kinds of ion channel proteins, and the ion channel proteins distribute in substantially all the cells. Thus, these ion channel proteins are likely to cause the disease, and it is said that 30 to 40% of targets in making a drug are ion channel proteins. Generally, a pharmacological test is carried out to confirm an effect obtained by administering a reagent to an experimental animal. If it is possible to form a stable artificial lipid bilayer membrane 2, it is possible to carry out screening in making a drug while directly examining an effect exerted to a target ion channel. Particularly, most of drugs such as psychoactive drugs for acting upon a nerve system directly act upon the ion channel proteins, so that the current measuring device can be favorably adopted to the drug making in this field. Adversely, the current measuring device can be used to select a substance which does not act upon the human ion channel in making an agrichemical.

Further, the current measuring device according to the present invention can be used to carry out visual analysis of protein-protein (drug) interaction on the artificial lipid bilayer membrane. Moreover, by changing a type of molecules included in the artificial lipid membrane, it is possible to apply the current measuring device to detection of various substances.

Embodiment 2

Figure 4:
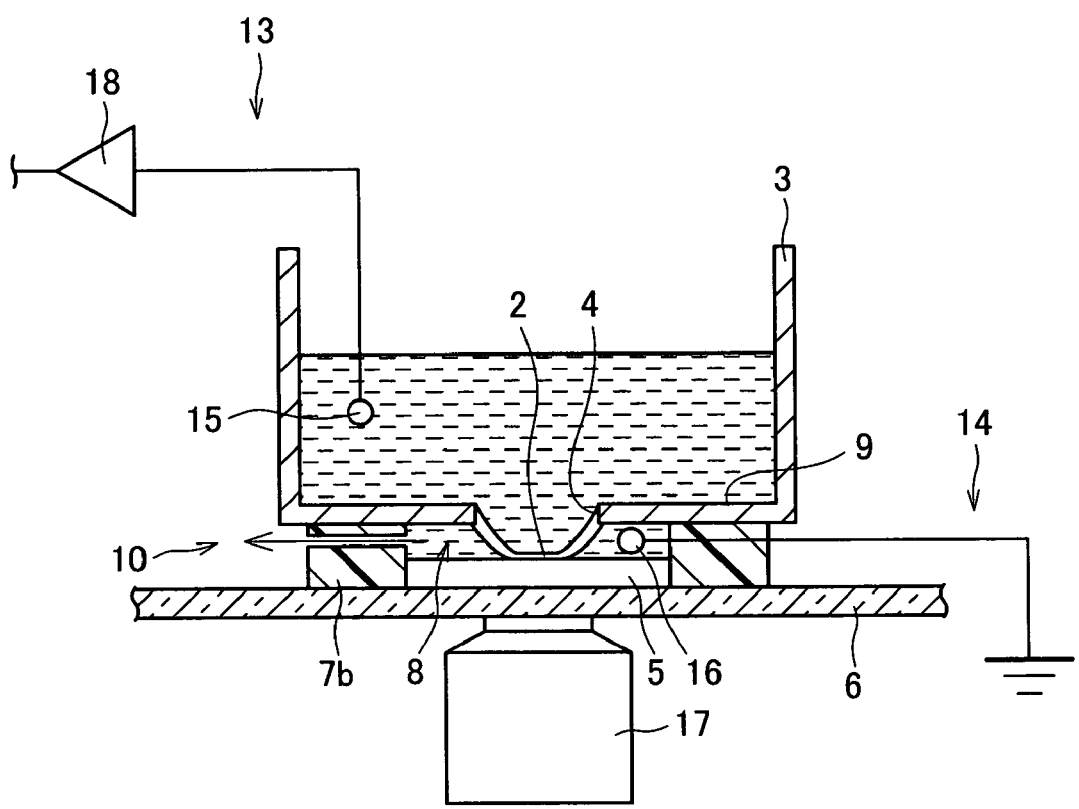
FIG. 4 is a cross sectional view schematically illustrating another structure of the current measuring device according to the present invention.
Figure 5:
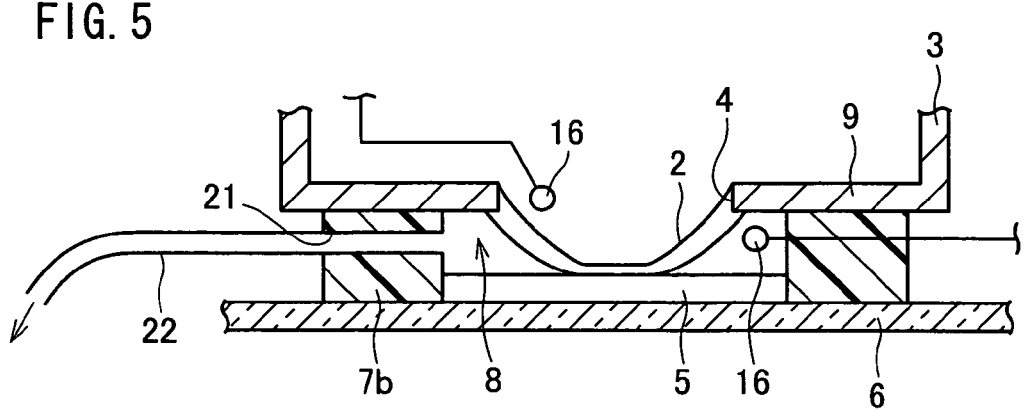
FIG. 5 is a partial cross sectional view more specifically illustrating a negative pressure sucking section of the current measuring device illustrated in FIG. 4.
Figure 6:
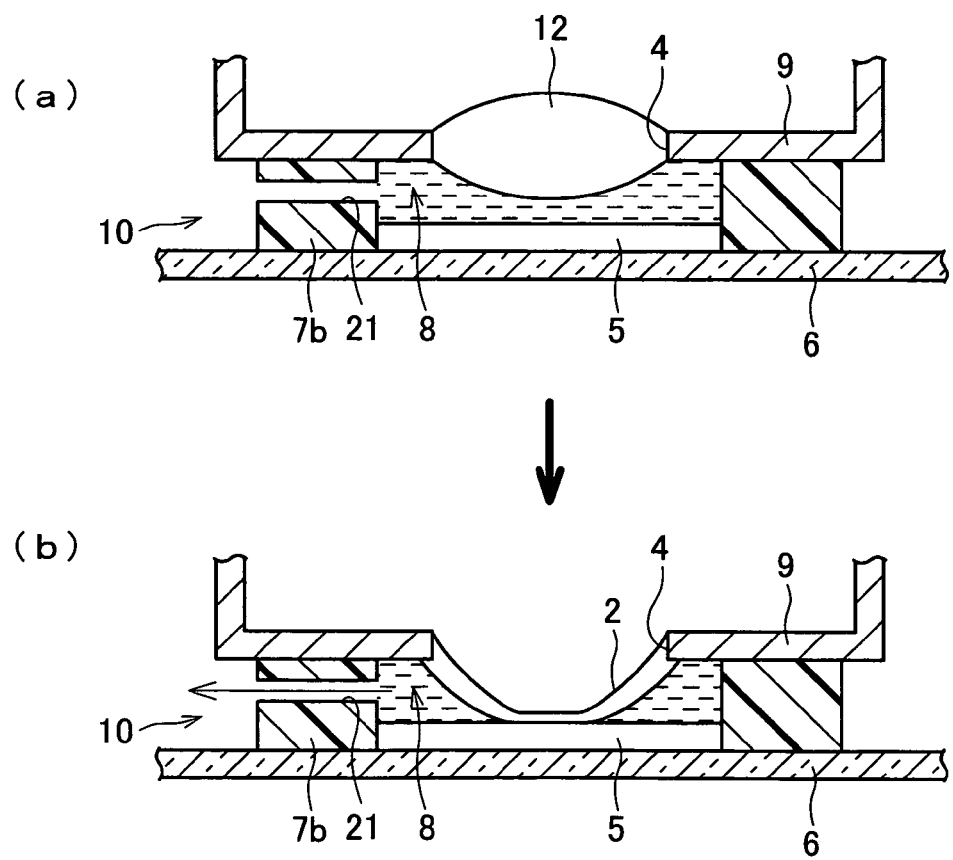
In FIG. 6, (a) is a partial cross sectional view illustrating a state in which the lipid solution is applied to the small hole of the upper solution chamber in the current measuring device of FIG. 1.
Figure 7:
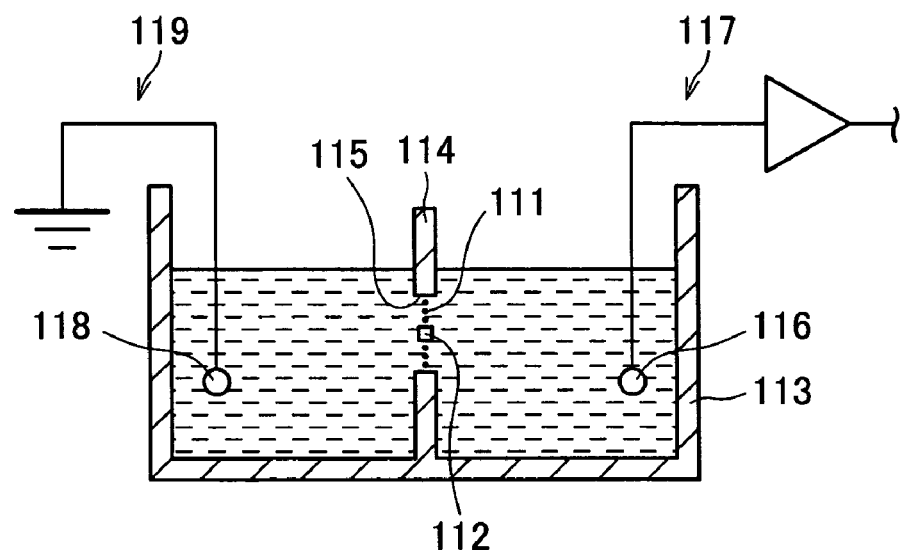
FIG. 7 is a schematic illustrating a conventional planar lipid bilayer method.
Figure 8:
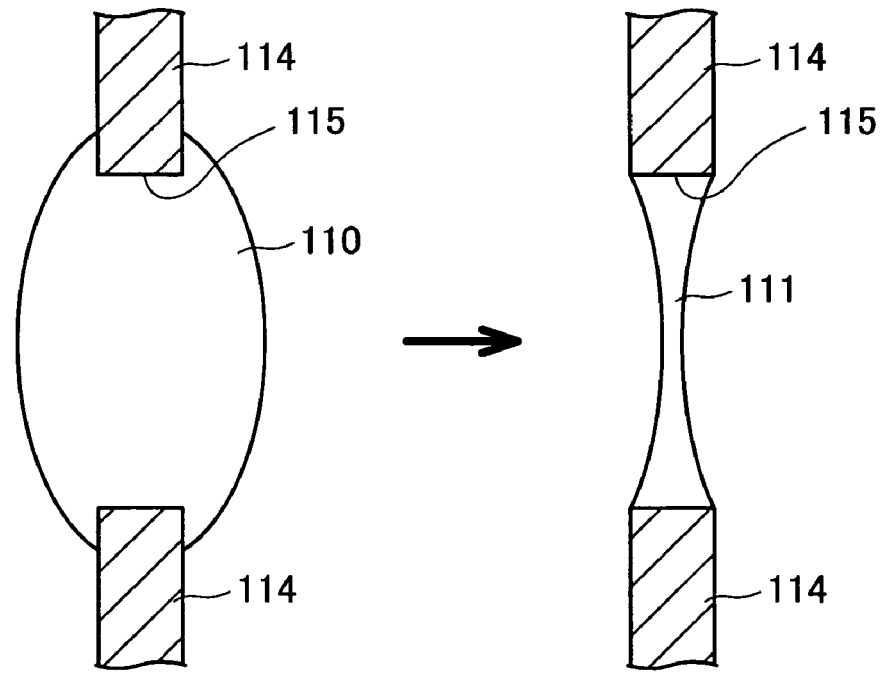
FIG. 8 illustrates a conventional vertical painting method.
Figure 9:
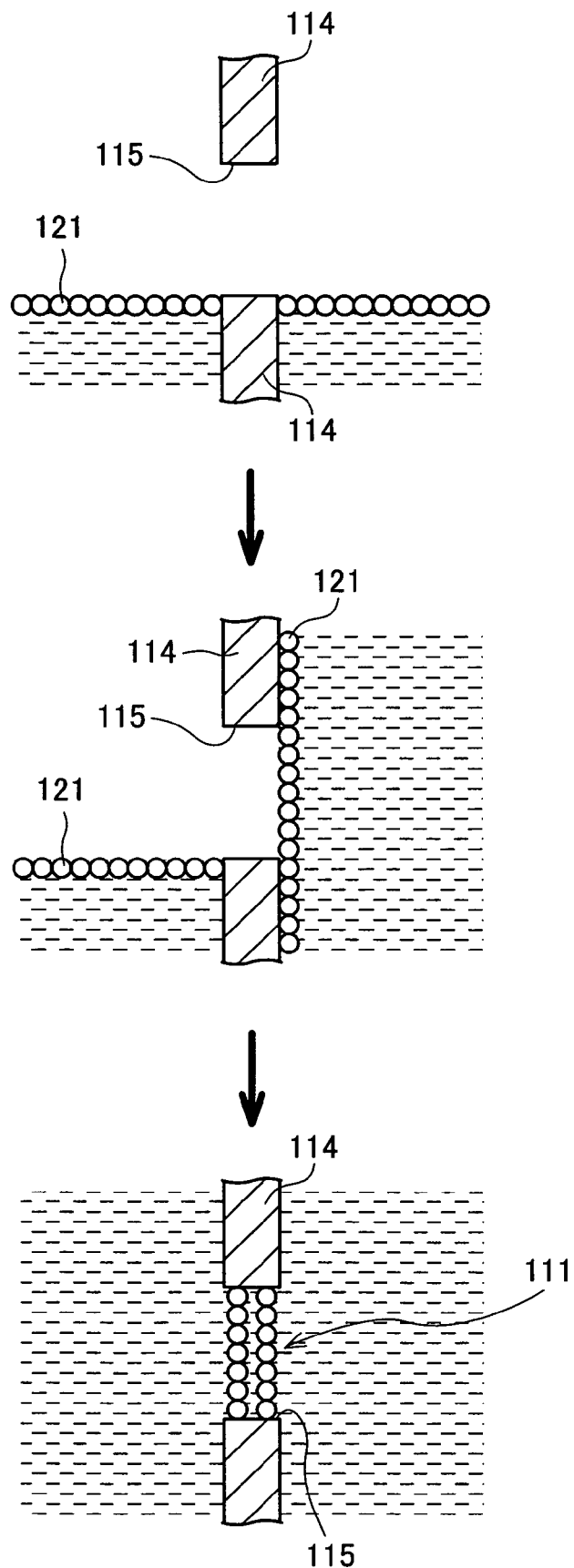
FIG. 9 illustrates a conventional vertical applying method.
Figure 10:
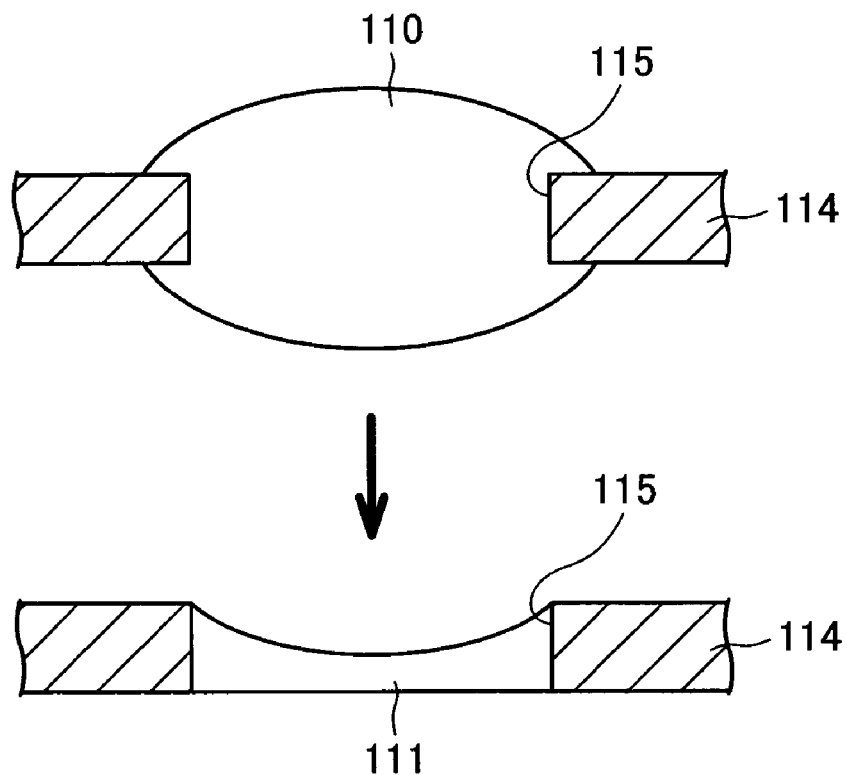
FIG. 10 (a) shows a horizontal formation method.
Figure 10:
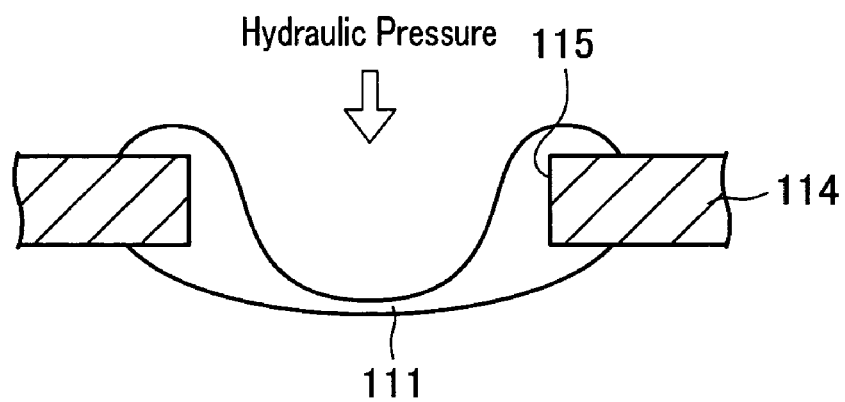
Figure 11:
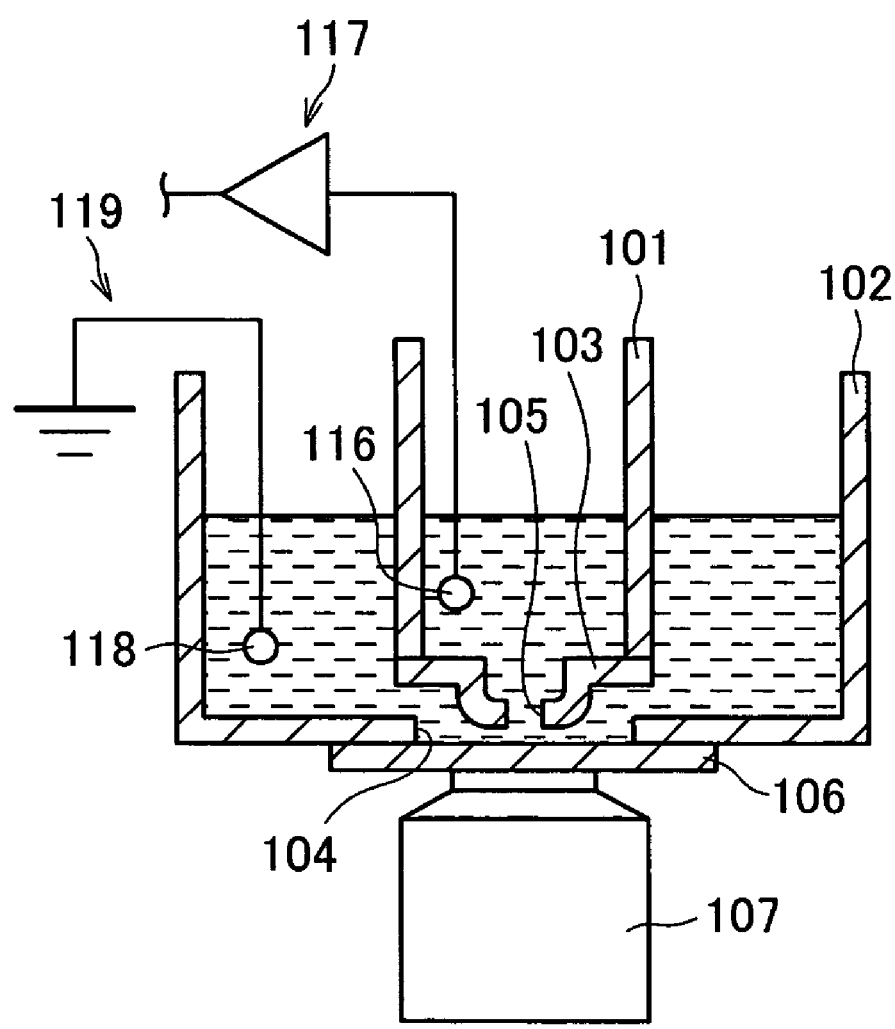
FIG. 11 illustrates a current measuring device having a conventional artificial lipid bilayer membrane.

The following explains another embodiment of the present invention with reference to FIG. 4 to FIG. 6. Note that, the present invention is not limited only to recitations of the present embodiment. Further, explanations of members and the like having the same functions and effects as those of members explained in Embodiment 1 are omitted.

FIG. 4 is a cross sectional view schematically illustrating another current measuring device according to the present invention. FIG. 5 is a cross sectional view more specifically illustrating a structure of a negative pressure generation section shown in FIG. 4. In FIG. 6, (a)and (b) are cross sectional views each of which illustrates a state in which an artificial lipid bilayer membrane is formed in the current measuring device illustrated in FIG. 4.

(1) Another Example of the Current Measuring Device Having the Artificial Lipid Bilayer Membrane As illustrated in FIG. 4, the current measuring device according to the present embodiment is arranged basically in the same manner as the current measuring device described in Embodiment 1, but is different from the current measuring device of Embodiment 1 in that: the interval keeping member 7a cannot change the interval, and a negative pressure generation section (negative pressure generation means) 10 for generating a negative pressure in the lower solution chamber 8.

<Interval Keeping Member>

A basic shape of the interval keeping member 7b used in the present embodiment is the same as the shape of the interval keeping member 7a used in Embodiment 1 but is not arranged so as to be movable in upward and downward directions. Thus, a material of the interval keeping member 7b is not particularly limited as long as the material can be tightly in contact with the upper solution chamber 3 and the bottom plate 6 and can tightly close the lower solution chamber 8. Specific favorable examples thereof include: silicone rubber such as polydimethylsiloxane (PDMS); epoxy resin; latex rubber; and the like.

<Negative Pressure Generation Section>

The negative pressure generation section 10 is not particularly limited as long as it is possible to adjust an internal pressure of the lower solution chamber 8 surrounded by the bottom plate 6 and the interval keeping member 7b so that the internal pressure is lower than the pressure in the upper solution chamber 3. However, an example of the arrangement of the negative pressure generation section 10 is as follows: as illustrated in FIG. 4, a hole is provided in a side wall of the interval keeping member 7b, and aqueous solution in the lower solution chamber 8 is sucked via the hole so as to generate a negative pressure.

A more specific structure of the negative pressure generation section 10 is not particularly limited. An example thereof is as follows: as illustrated in FIG. 5, the interval keeping member 7b is provided with a suction port 21 which allows connection between the lower solution chamber 8 and the outside of the current measuring device, and a tube 22 is connected to the suction port 21 so as to be drawn from the lower solution chamber 8 to the outside of the current measuring device, and a sucking section (sucking means: not shown) is connected via the tube 22. On this account, the sucking section sucks the aqueous solution from the lower solution chamber 8 via the suction port 21 and the tube 22 so as to drop the internal pressure of the lower solution chamber 8.

A specific structure of the suction port 21 is not particularly limited as long as the suction port 21 has a diameter which allows the aqueous solution in the lower solution chamber 8 to be sucked out so as to favorably drop the internal pressure of the lower solution chamber 8. Further, a method for forming the suction port 21 is not particularly limited as long as an appropriate method is selected in accordance with a material, a size, and the like of the interval keeping member 7b.

A specific structure of the tube 22 is not particularly limited as long as the tube 22 has a strength, a diameter, and a length which allow the sucking section to sufficiently suck the aqueous solution from the lower solution chamber 8. A material of the tube 22 is not particularly limited, but specific examples thereof include: fluorine resin such as polytetrafluoroethylene; silicone; and the like.

A specific structure of the sucking section is not particularly limited as long as it is possible to suck the aqueous solution from the lower solution chamber 8 via the suction port 21 and the tube 22. Specific examples thereof include a pipette, a dropper, a syringe, and the like. Also a material of the sucking section is not particularly limited as long as a suitable material is selected in accordance with the specific structure of the sucking section. For example, in the present invention, particularly a dropper made of silicone rubber can be favorably used.

Of course, the specific structure of the negative pressure generation section is not limited to the foregoing structure, and any known means can be favorably adopted as long as the means can reduce the pressure in the lower solution chamber 8.

(2) How to Form the Artificial Lipid Bilayer Membrane

Next, with reference to FIG. 6(*a*) and (*b*), the following explains how to form the artificial lipid bilayer membrane 2 on the small hole 4 provided in the bottom of the upper solution chamber 3 in the current measuring device according to the present embodiment.

First, the upper solution chamber 3 and the lower solution chamber 8 are filled with the aqueous solution. Next, as illustrated in FIG. 6(*a*), the lipid solution 12 is applied to the small hole 4. Thereafter, as illustrated in FIG. 6(*b*), via the suction port 21 which allows connection between the lower solution chamber 8 and the outside, the aqueous solution is sucked from the lower solution chamber 8 by using (i) the tube 22 connected to the suction port 21 and (ii) the sucking section (both of which are not illustrated in FIG. 6). On this account, the aqueous solution in the upper solution chamber 3 flows via an upper portion of the artificial lipid bilayer membrane 2 into the lower solution chamber 8, so that the artificial lipid bilayer membrane 2 swells downwardly. In this manner, the artificial lipid bilayer membrane 2 comes into contact with the support layer 5 so as to be thinner.

By differentiating the pressure in the upper solution chamber 3 from the pressure in the lower solution chamber 8 in this manner, it is possible to form the artificial lipid bilayer membrane 2 in several seconds unlike the case were there is no difference in the pressure. Further, according to the method of the present embodiment, it is possible to more easily differentiate the pressures from each other than the case where the pressure in the upper solution chamber 3 is raised so as to differentiate the pressures. Further, as described in the item (2) of Embodiment 1, unlike the case where the pressure in the upper solution chamber 3 is raised so as to swell the artificial lipid bilayer membrane 2 to the side of the lower solution chamber, according to the method of the present embodiment, it is possible to form the stable artificial lipid bilayer membrane 2, and it is possible to solve such problem that a larger device is required in forming the artificial lipid bilayer membrane whose area size is small. Further, the upper solution chamber 3 is open, and the lower solution chamber 8 is tightly closed by the artificial lipid bilayer membrane 2, the bottom 9 of the upper solution chamber 3, the interval keeping member 7*a*, and the bottom plate 6. Thus, the artificial lipid bilayer membrane 2 is stabilized in a direction parallel to the bottom plate 6 which was conventionally instable, so that it is possible to further improve the durability of the artificial lipid bilayer membrane 2.

Thus, the present invention includes the method for forming the artificial lipid bilayer membrane 2 in the foregoing manner. Specifically, in the artificial lipid bilayer membrane formation method according to the present invention, the upper solution chamber 3 whose bottom 9 has a membrane formation opening (small hole 4) and the lower solution chamber 8 are used. The lower solution chamber 8 is disposed below the upper solution chamber 3, and includes: the bottom plate 6 placed on the surface of the support layer 5 for supporting the artificial lipid bilayer membrane 2; and the interval keeping member 7*b* for keeping a predetermined interval between the upper solution chamber 3 and the bottom plate 6, and the lower solution chamber 8 is provided so as to be surrounded by the bottom plate 6 and the interval keeping member 7*b*. Here, the lower solution chamber 8 is provided with a negative pressure generation section (negative pressure generation means 10) for dropping the internal pressure of the lower solution chamber 8. The artificial lipid bilayer membrane formation method according to the present invention includes the steps of: (i) applying the lipid solution 12 to the membrane formation opening (small hole 4) under such condition that surfaces of the membrane formation opening (small hole 4) which are respectively positioned on the side of the upper solution chamber 3 and the side of the lower solution chamber 8 are in contact with the aqueous solution; and (ii) dropping the internal pressure of the lower solution chamber 8 by using the negative pressure generation means (negative pressure generation section 10) so as to make the artificial lipid bilayer membrane 2 thinner.

Also in the present embodiment, as in Embodiment 1, it is possible to quickly form the artificial lipid bilayer membrane 2, and it is possible to further stabilize the formed artificial lipid bilayer membrane 2. Therefore, also the current measuring device according to the present embodiment can be used in the same manner as in Embodiment 1.

Note that, the interval keeping member 7*b* in the present embodiment may be arranged so as to include only the negative pressure generation section 10. However, as in Embodiment 1, the interval keeping member 7*b* may be arranged so as to include also a function for changing the interval between the upper solution chamber 3 and the bottom plate 6. That is, the interval keeping member 7*b* may be made of elastic material and may be arranged so as to reduce the pressure in the lower solution chamber 8 and be capable of changing the interval.

EXAMPLES

With reference to Examples, FIG. 3, FIG. 5 to FIG. 13 to FIG. 17, the following further details the present invention, but the present invention is not limited to them.

In the present Example, a current measuring device according to the present invention (FIG. 5) was used. As illustrated in FIG. 5, a propylene chamber whose volume was 0.1 cm$^3$ and bottom thickness (bottom 9) was 0.2 mm to 0.3 mm was used as the upper solution chamber 3. In the bottom 9, a small hole 4 whose diameter was 0.15 mm was provided. A square glass plate whose thickness was 0.17 mm and each side was 18 mm was used as the bottom plate 6. Further, an agarose gel layer whose thickness was 100 nm was formed on the bottom plate 6 as the support layer 5 so as to be positioned in a face contacting the upper solution chamber 3. The agarose gel layer was formed as follows: agarose dispersion liquid made of agarose (product of Sigma) was prepared, and the thus prepared liquid was heated so that agarose was dissolved, and then the liquid was applied to the bottom plate 6, and the applied liquid was dried at a room temperature. As the interval keeping member 7*b*, a material whose upper and lower portions were open and whose internal portion has a hollowed cylindrical shape as illustrated in FIG. 3 was used. An internal diameter of the interval keeping member 7*b* was 1.0 mm, and a height of the interval keeping member 7*b* was 0.2 mm. Further, the interval keeping member 7*b* was made of silicone rubber. The interval keeping member 7*b* was provided with a suction port 21 and a polytetrafluoroethylene tube 22 which was connected to the suction port 21 and had a diameter of 50 μm or less. To the polytetrafluoroethylene tube 22, a dropper made of silicone rubber was connected. As the electrode 16, an Ag—AgCl electrode obtained by plating an Ag foil with Ag was used. Further, as the Ag—AgCl electrode of the lower solution chamber 8, an electrode in which silicone rubber was provided at the time of silicone rubber formation was used. In measuring a current, a patch-clamp amplifier (CEZ-2400 produced by Nihon Kohden Corporation) was used, and the measured current was recorded on a DAT tape by using a DAT recorder.

Example 1

Current Measurement of Plain Muscle $Ca^{2+}$ Dependency $K^+$ Channel

First, the upper solution chamber 1 and the lower solution chamber 2 were filled with aqueous solution made of 100 mM KCl, $10^{-9}$ M $CaCl_2$, 10 mM Hepes (pH 7.4).

Thereafter, lipid solution obtained by dissolving phosphatidylcholine (product of Sigma) in decane so that its concentration was 20 mg/mL was applied to the small hole 4 provided in the bottom 9 of the upper solution chamber 3. After the application, the dropper was used to suck the aqueous solution from the upper solution chamber 8 so that the artificial lipid bilayer membrane 2 was swollen to the side of the lower solution chamber 8, thereby forming the artificial lipid bilayer membrane 2. Through a microscope, it was observed that the artificial lipid bilayer membrane 2 was formed. Next, a cell membrane vesicle sampled from a bovine tracheal plain muscle was fused with the artificial lipid bilayer membrane 2, thereby inserting a $K^+$ channel on the vesicle membrane into the artificial lipid bilayer membrane 2, thereby producing the current measuring device of the present invention. By using the thus produced current measuring device, a current was measured with time.

Subsequently, only the $CaCl_2$ concentration of the aqueous solution with which the upper solution chamber 3 and the lower solution chamber 8 were filled was changed into 1 mM. Under this condition, a current measuring device was produced in the same manner, and a current was measured.

Figure 13:
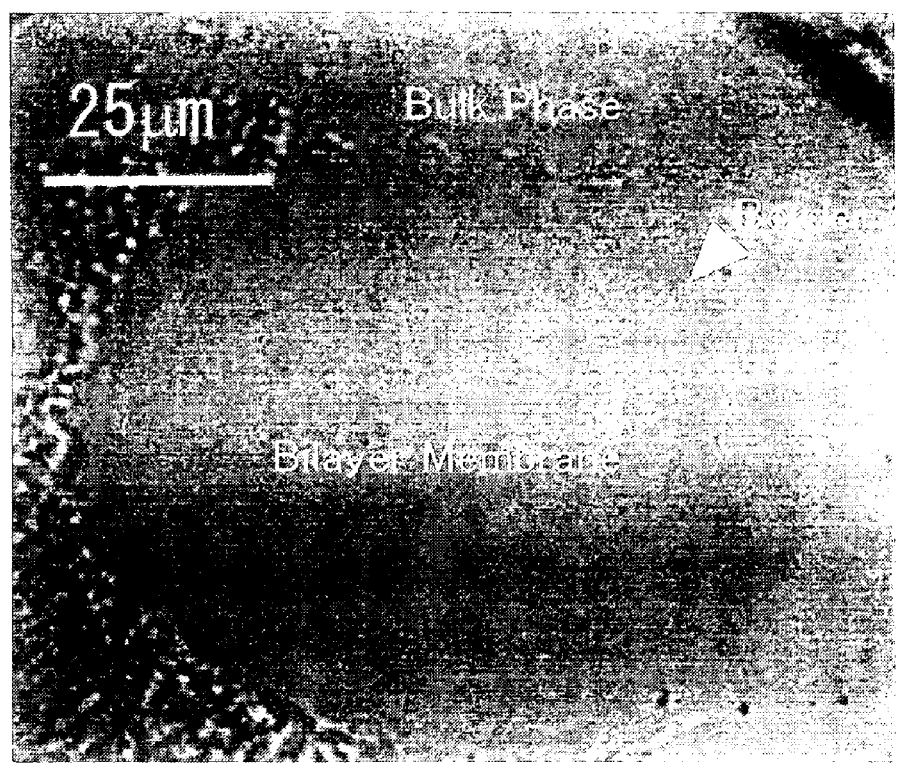
FIG. 13 is a photograph showing a state in which making an artificial lipid bilayer membrane thinner is completed in Example 1.
Figure 14:
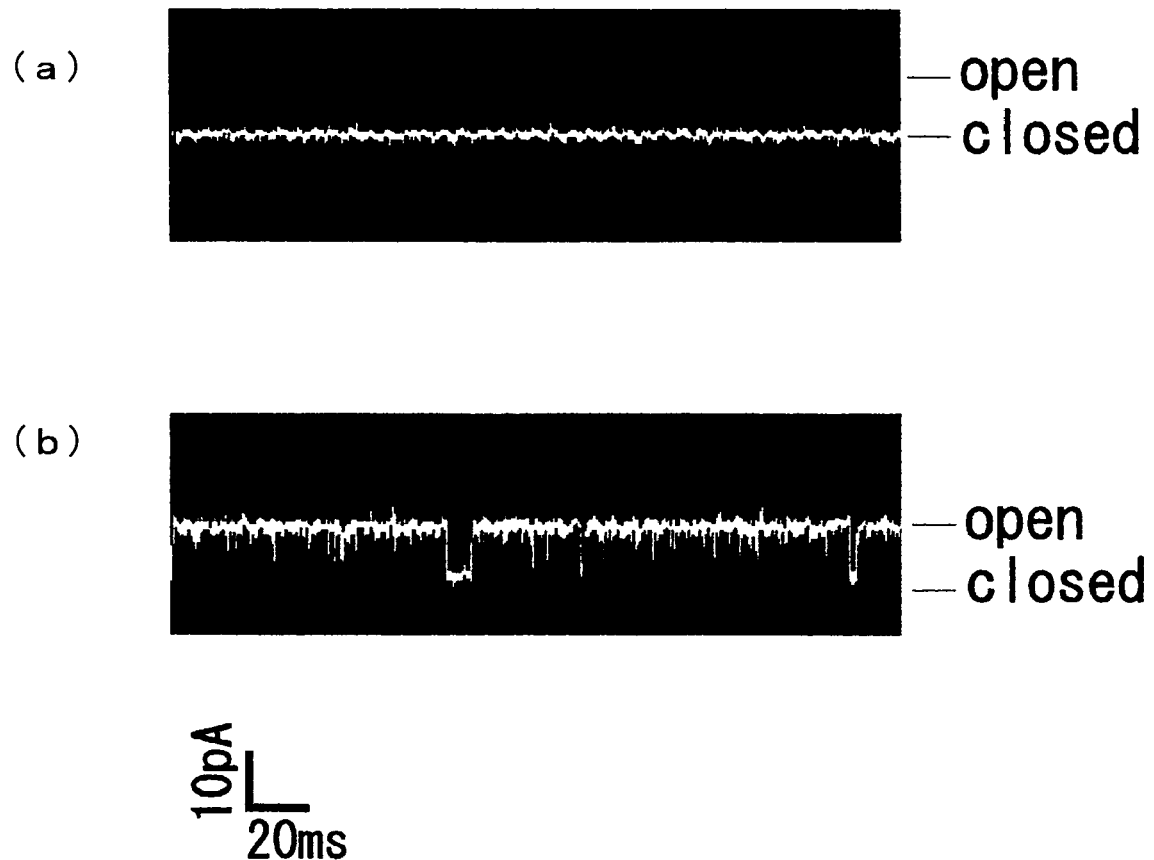
FIG. 14 (a) illustrates a trace of the current in case where the aqueous solution includes 100mM KCl and $10^{-9}$M $CaCl_2$.
Figure 15:
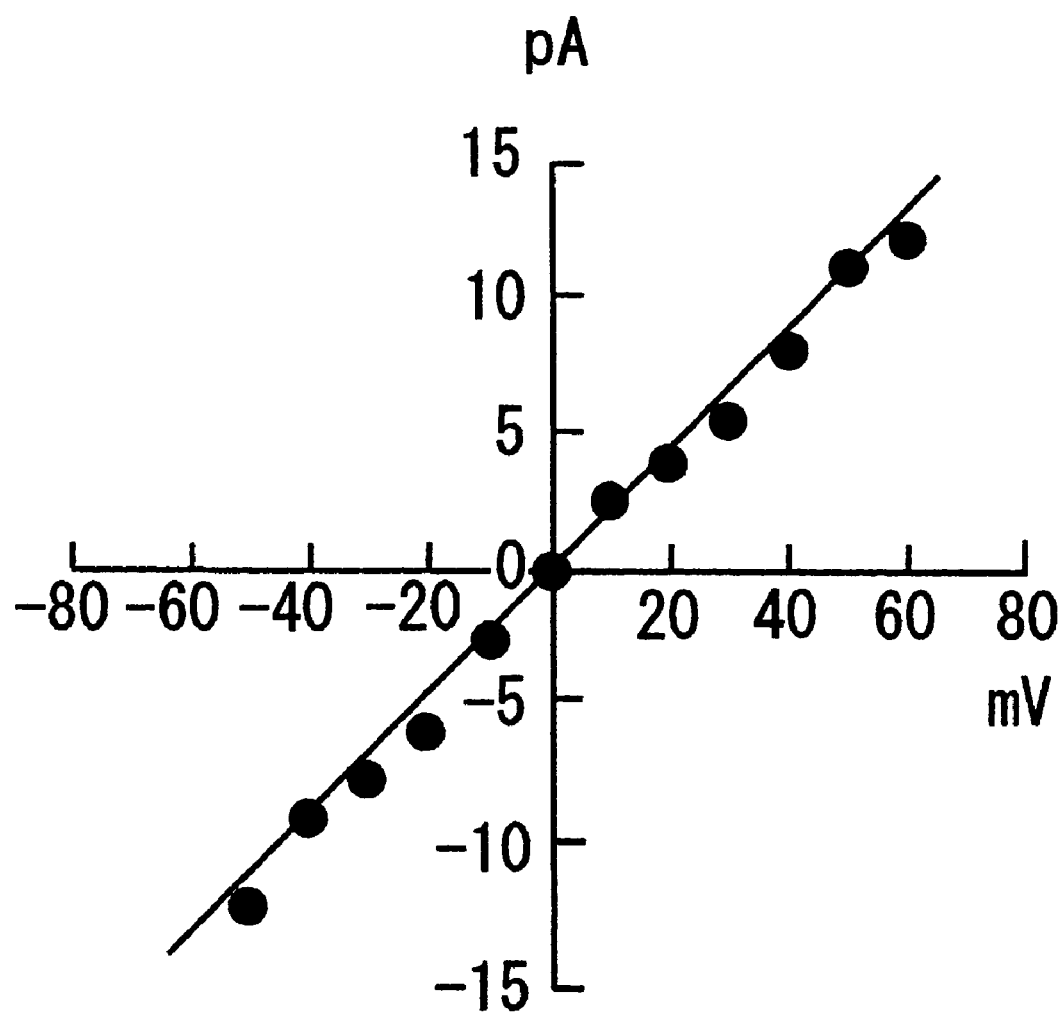
FIG. 15 illustrates a membrane potential-current property measured in Example 1.

FIG. 13 illustrates a state in which the formed artificial lipid bilayer membrane 2 has been completely made thinner. A border between the artificial lipid bilayer membrane 2 (referred to as "bilayer membrane" in FIG. 13) and its peripheral cyclic bulk phase (referred to as "bulk phase" in FIG. 13) can be recognized. This shows that making the lipid solution thinner was completed. FIG. 14 illustrates the thus obtained trace of the current, and FIG. 15 illustrates a membrane potential-current property. In FIG. 14, (a) illustrates a trace of the current in case where the aqueous solution includes 100 mM KCl and $10^{-9}$ M $CaCl_2$. In FIG. 14, (b) illustrates a trace of the current in case where the aqueous solution includes 100 mM KCl and 1 mM $CaCl_2$. It was confirmed that: when the concentration of $CaCl_2$ was $10^{-9}$ M, the ion channel was closed; and when the concentration of $CaCl_2$ was 1 mM, the ion channel is more likely to open. A pattern of the thus obtained trace of the current was the same as a pattern having been obtained as a result of a conventional experiment. This shows that: by using the current measuring device of the present invention, it is possible to quickly and easily form a stable artificial lipid bilayer membrane 2, so that it is possible to obtain a reliable result of the current measurement. Further, a value of a single channel current (inductance of a single channel) obtained from an inclination indicated by an I-V line of FIG. 15 was 220 pS ($=220\times10^{-12}$ A/V). This value was identical with a value obtained in a conventional method such as an artificial bilayer method, a patch-cramp method, and the like. This shows that: the current measuring device of the present invention can exactly measure a property of a biological membrane ion channel. Further, this shows that the current measuring device of the present invention can measure a current so that the agarose gel layer under the artificial lipid bilayer membrane has no influence on an ion channel or a current measuring system.

Example 2

Simultaneous Measurement of Formation of a Channel Pore (Optical Observation) and a Single Channel Current Based on Antibiotic Alamethicin Instead of vesicle used in Example 1, a methanol solution of alamethicin (product of Sigma) fluorescence-labeled with Cy3 (product of Amensham Pharmacia) was added to the aqueous solution of the upper solution chamber 3 so that its final concentration was about $10^{-8}$ M. The fluorescence labeling of alamethicin was carried out as follows: glycine was added to a C end of alamethicin, and Cy3 was fixed on an amino group of glycine with a Cy3 mono functional dye kit (product of Amensham Pharmacia) so that glycine and Cy3 were combined with each other. Alamethicin was amphipathic peptide and moved from the liquid phase to the artificial lipid bilayer membrane 2 in a natural manner so as to form an ion channel. Note that, as the aqueous solution with which the upper and lower solution chambers were filled, aqueous solution of 100 mM KCl and 10 mM Hepes (pH 7.4) was used.

By using the current measuring device of the present invention, the fluorescent image and an ion current based on alamethicin were simultaneously observed and measured. Note that, the fluorescent image was observed through a total internal reflection fluorescence microscope of the inventors' own composition.

Figure 16:
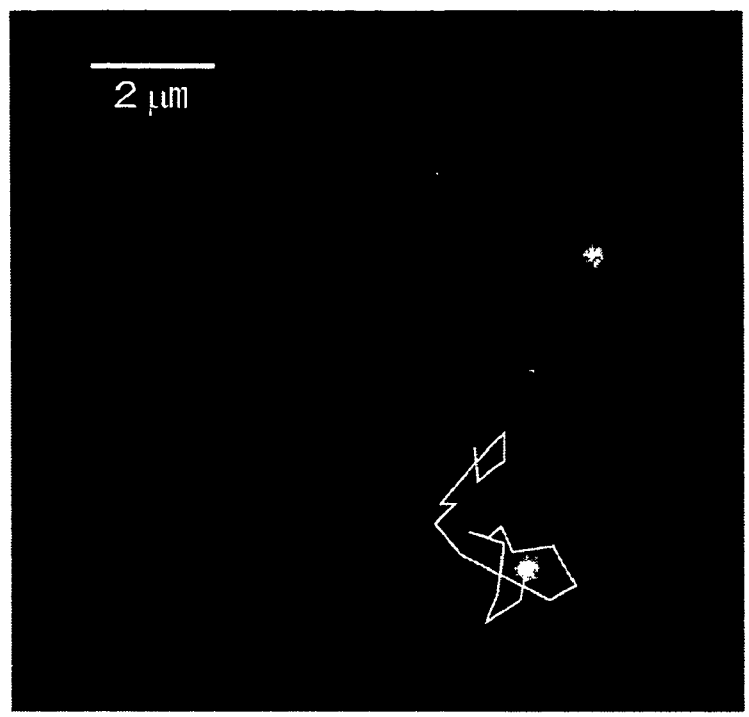
In FIG. 16, (a) illustrates a fluorescent image obtained by fluorescence-labeling alamethicin in Example 2.
Figure 16:
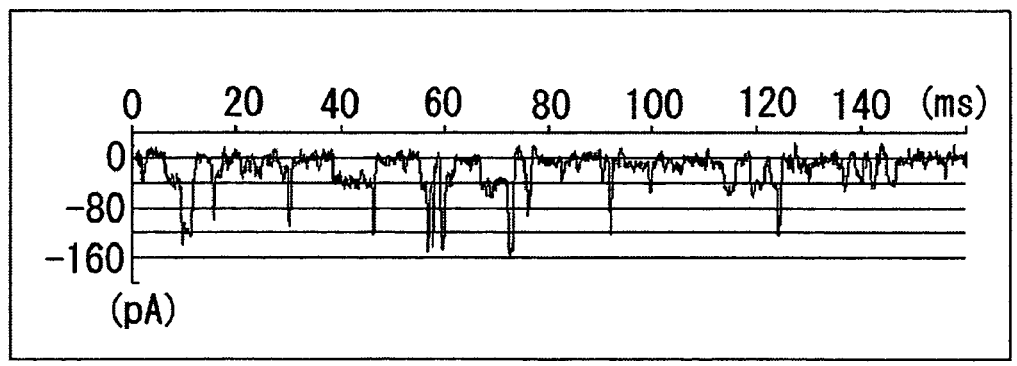

In FIG. 16, (a) illustrates the obtained fluorescent image of fluorescent alamethicin and a line indicative of Brownian motion in the membrane. In FIG. 16, (b) illustrates a current trace. By using the current measuring device of the present invention in this manner, it is possible to simultaneously carry out measurement of an ion current and optical observation of an ion channel.

Example 3

Detection of Ryanodine

First, the upper solution chamber 3 and the lower solution chamber 8 were filled with aqueous solution of 500 mM Na-methanesulfonic acid, 40 mM Hepes (pH 7.4), 0.01-0.1 μM $Ca^{2+}$.

Thereafter, solution obtained by dissolving phosphatidylcholine in decane so that its concentration was 20 mg/ml was applied to the small hole 4 provided in the bottom 9 of the upper solution chamber 3. Then, the dropper was used to suck the aqueous solution in the lower solution chamber 8 so that the artificial lipid bilayer membrane 2 swelled to the side of the lower solution chamber 8, thereby forming the artificial lipid bilayer membrane 2. Next, a cell membrane vesicle sampled from a swine cardiac muscle was fused with the artificial lipid bilayer membrane, thereby inserting a ryanodine receptor channel (Ca- channel) on the vesicle membrane into the artificial lipid bilayer membrane 2. At this time, the ryanodine receptor channel on the vesicle membrane was fluorescence-labeled with fluorescent dye Cy5 (product of Amensham Pharmacia) in advance, and then the cell membrane vesicle was fused with the artificial lipid bilayer membrane 2. The fluorescence labeling of the ryanodine receptor channel was carried out as follows: a corresponding specific monoclonal antibody was labeled with Cy5, and the thus labeled antibody was coupled with the ryanodine receptor channel.

While measuring a single channel current by using the obtained current measuring device of the present invention, ryanodine (product of Sigma) of 1 to 10 nM fluorescence-labeled with Cy5 (product of Amensham Pharmacia) was added from the upside of the membrane, and channel activity was observed.

Figure 17:
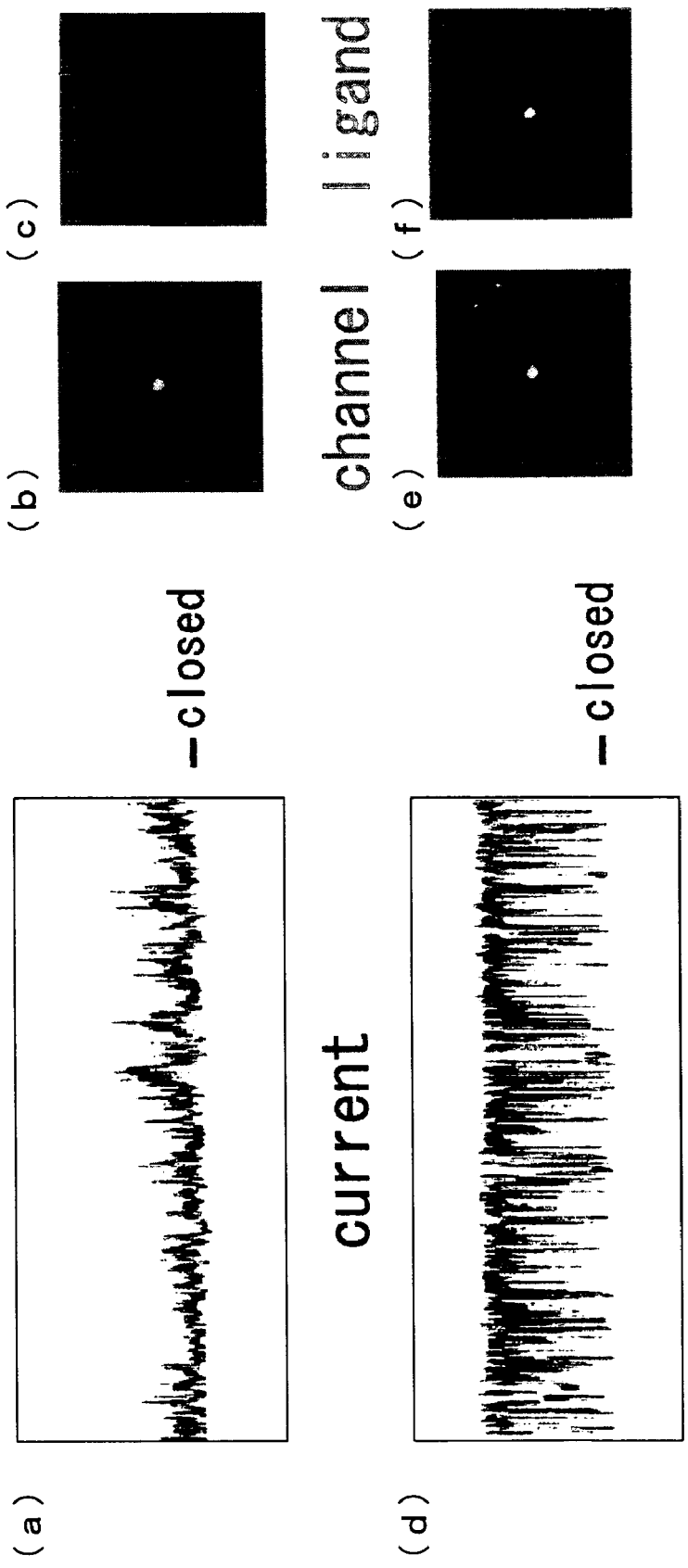
In FIG. 17, (a) illustrates a current trace measured or observed before addition of ryanodine in Example 3.

In FIG. 17, (a) illustrates a current trace before addition of ryanodine (in this Figure, the trace is indicated as "current", and this is the same as in (b)). In FIG. 17, (b) illustrates a fluorescent image of the ryanodine receptor channel (in this Figure, the image is indicated as "channel", and this is the same as in (e)). In FIG. 17, (c) illustrates a fluorescent image of ryanodine (in this Figure, the image is indicated as "ligand", and this is the same as in (f). In FIG. 17, (d) illustrates a current trace after addition of ryanodine. In FIG. 17, (e) illustrates a fluorescent image of the ryanodine receptor channel. In FIG. 17, (f) illustrates a fluorescent image of ryanodine. By observing the ryanodine receptor channel and the fluorescent image of ryanodine and measuring a current at the same time, it is possible to simultaneously observe ryanodine and confirm that activation of the ryanodine receptor channel occurs.

As described above, a current measuring device according to the present invention, which is capable of measuring a current flowing via an artificial lipid bilayer membrane, includes: an upper solution chamber which is capable of containing aqueous solution; and a lower solution chamber disposed below the upper solution chamber, a bottom of the upper solution chamber having a membrane formation opening, a bottom of the lower solution chamber having a support layer for supporting the artificial lipid bilayer membrane, the artificial lipid bilayer membrane formed on the membrane formation opening of the upper solution chamber being brought into contact with the support layer so as to be supported, and the current measuring device further includes: a bottom plate on which the support layer is placed; and an interval keeping member for keeping a predetermined interval between the upper solution chamber and the bottom plate, wherein the lower solution chamber is provided below the upper solution chamber by being surrounded with the bottom plate and the interval keeping member, and the artificial lipid bilayer membrane formed on the membrane formation opening is swollen to a side of the lower solution chamber so as to be made thinner and come into contact with the support layer so that the artificial lipid bilayer membrane is supported on the support layer.

Further, the current measuring device according to the present invention may be arranged so as to be capable of measuring a current flowing via an artificial lipid bilayer membrane, and the current measuring device includes: an upper solution chamber which is capable of containing aqueous solution and whose bottom has a membrane formation opening; and a lower solution chamber which is disposed below the upper solution chamber and which is capable of containing the aqueous solution, wherein the lower solution chamber is constituted of (i) a bottom plate and (ii) an interval keeping member for bringing a bottom of the upper solution chamber and the bottom plate tightly into contact with each other so that a predetermined interval between the upper solution chamber and the bottom is kept, and the bottom plate has a support layer for supporting the artificial lipid bilayer membrane.

Further, in the foregoing arrangement, the artificial lipid bilayer membrane formed on the membrane formation opening of the upper solution chamber is swollen to the side of the lower solution chamber so that the artificial lipid bilayer membrane becomes thinner and comes into contact with the support layer so as to be supported on the support layer.

According to the foregoing arrangement, the lower solution chamber is not open, so that vibration caused by the aqueous solution flow is suppressed, so that it is possible to form the artificial lipid bilayer membrane which is stable also in a direction parallel to the bottom of the upper solution chamber.

Further, the current measuring device according to the present invention is arranged so as to include negative pressure generation means for dropping an internal pressure of the lower solution chamber provided by being surrounded with the bottom plate and the interval keeping member, wherein the negative pressure generation means causes the artificial lipid bilayer membrane formed on the membrane formation opening of the upper solution chamber to swell to the side of the lower solution chamber. It is preferable that the negative pressure generation means is formed in the interval keeping member and includes (i) a suction port which allows connection between the lower solution chamber and an outside and (ii) sucking means which is connected to the suction port so as to suck the aqueous solution in the lower solution chamber.

Further, the current measuring device according to the present invention may be arranged so that the interval keeping member is capable of changing an interval between the upper solution chamber and the bottom plate, and the change of the interval causes the artificial lipid bilayer membrane formed on the membrane formation opening of the upper solution chamber to swell to the side of the lower solution chamber. In this case, it is preferable that the interval keeping member is made of an elastic material so as to be capable of expanding and contracting upward and downward.

According to the foregoing arrangement, by dropping the internal pressure of the lower solution chamber, it is possible to quickly and easily form the artificial lipid bilayer membrane in short time such as several seconds.

Further, in the current measuring device according to the present invention, it is preferable that the support layer is made of polymer gel, and it is more preferable that agarose or polyacrylamide is used. Further, it is preferable that a thickness of the support layer made of the polymer gel is 50 nm or more and 2 mm or less.

According to the foregoing arrangement, even when the internal pressure of the lower solution chamber is dropped, the artificial lipid bilayer membrane is supported by the polymer gel layer, so that the artificial lipid bilayer membrane is stabilized in upward and downward directions.

Further, it is preferable to arrange the current measuring device according to the present invention so that a diameter of the membrane formation opening is 10 μm or more and 500 μm or less.

Further, it is preferable to arrange the current measuring device according to the present invention so that the bottom plate is made of a translucent material, and optical observation means which allows observation of the artificial lipid bilayer membrane on the support layer is provided below the bottom plate.

Further, it is preferable to arrange the current measuring device according to the present invention so as to include: current measuring means electrically connected to the upper solution chamber; and earthing means electrically connected to the lower solution chamber.

As described above, by using the current measuring device according to the present invention, it is possible to easily form the highly durable artificial lipid bilayer membrane 2 which is stable also in a direction parallel to the bottom 9 of the upper solution chamber 3. Further, it is possible to measure a channel current and optically observe an ion channel at the same time. Moreover, the current measuring device can be made smaller, so that it is possible to manufacture a smaller sensor by providing the current measuring device on a small-size chip.

As a result, by changing a type of the ion channel, it is possible to apply the foregoing technique to detection of various substances, so that the present invention is usable in screening a drug made by using an ion channel protein concerning a disease. Further, by simultaneously carrying out the channel current measurement and the optical observation, it is possible to favorably use the present invention also in clarifying a relation of an ion channel function and an ion channel structure.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

INDUSTRIAL APPLICABILITY

The current measuring device according to the present invention is usable in screening a drug made by using an ion channel protein concerning a disease for example.

There are many kinds of ion channel proteins, and the ion channel proteins distribute in substantially all the cells. Thus, these ion channel proteins are likely to cause the disease, and it is said that 30 to 40% of targets in making a drug are ion channel proteins. Generally, a pharmacological test is carried out to confirm an effect obtained by administering a reagent to an experimental animal. If it is possible to form a stable artificial lipid bilayer membrane 2, it is possible to carry out screening in making a drug while directly examining an effect exerted to a target ion channel. Particularly, most of drugs such as psychoactive drugs for acting upon a nerve system directly act upon the ion channel proteins, so that the current measuring device can be favorably adopted to the drug making in this field. Adversely, the current measuring device can be used to select a substance which does not act upon the human ion channel in making an agrichemical.

Further, the current measuring device according to the present invention can be used to carry out visual analysis of protein-protein (drug) interaction on the artificial lipid bilayer membrane. Moreover, by changing a type of molecules included in the artificial lipid membrane, it is possible to apply the current measuring device to detection of various substances.

The invention claimed is:

1. A current measuring device, which is capable of measuring a current flowing via an artificial lipid bilayer membrane, comprising:
   an upper solution chamber which is capable of containing aqueous solution; and
   a lower solution chamber disposed below the upper solution chamber, a bottom of the upper solution chamber having a membrane formation opening, a bottom of the lower solution chamber having a support layer for supporting the artificial lipid bilayer membrane, wherein the artificial lipid bilayer membrane formed on the membrane formation opening of the upper solution chamber is brought into contact support layer so as to be supported,
   said current measuring device further including a bottom plate on which the support layer is placed; an interval keeping member for keeping a predetermined interval between the upper solution chamber and the bottom plate, and a negative pressure generation means for dropping an internal pressure of the lower solution chamber,
   wherein the lower solution chamber is provided below the upper solution chamber and surrounded by the bottom plate and the interval keeping member, and the negative pressure generation means causes the artificial lipid bilayer membrane formed on the membrane formation opening of the upper solution chamber to swell to a side of the lower solution chamber so as to cause the artificial lipid bilayer membrane to be thinner and to come into contact with the support layer so that the artificial lipid bilayer membrane is supported on the support layer.

2. The current measuring device as set forth in claim 1, wherein the negative pressure generation means is formed in the interval keeping member and includes (i) a suction port which allows connection between the lower solution chamber and an outside and (ii) sucking means which is connected to the suction port so as to suck the aqueous solution in the lower solution chamber.

3. The current measuring device as set forth in claim 1, wherein the support layer is made of polymer gel.

4. The current measuring device as set forth in claim 1, wherein a diameter of the membrane formation opening is 10 µm or more and 500 µm or less.

5. The current measuring device as set forth in claim 1, wherein the bottom plate is made of a translucent material, and optical observation means which allows observation of the artificial lipid bilayer membrane on the support layer is provided below the bottom plate.

6. The current measuring device as set forth in claim 1, further comprising: a current measuring means electrically connected to the upper solution chamber; and an earthing means electrically connected to the lower solution chamber.

7. The current measuring device as set forth in claim 1, wherein the artificial lipid bilayer membrane includes an ion channel.

8. A current measuring device, which is capable of measuring a current flowing via an artificial lipid bilayer membrane, comprising:
   an upper solution chamber which is capable of containing aqueous solution; and
   a lower solution chamber disposed below the upper solution chamber, a bottom of the upper solution chamber having a membrane formation opening, a bottom of the lower solution chamber having a support layer for supporting the artificial lipid bilayer membrane,
   wherein the artificial lipid bilayer membrane formed on the membrane formation opening of the upper solution chamber is brought into contact with the support layer so as to be supported,
   said current measuring device including a bottom plate on which the support layer is placed; and an interval keeping member for keeping a predetermined interval between the upper solution chamber and the bottom plate,
   wherein the lower solution chamber is provided below the upper solution chamber and surrounded by the bottom plate and the interval keeping member, and the interval keeping member is capable of changing an interval between the upper solution chamber and the bottom plate, and the change of the interval causes the artificial lipid bilayer membrane formed on the membrane formation opening of the upper solution chamber to swell to the side of the lower solution chamber so as to make the artificial lipid bilayer to be thinner and to come into contact with the support layer so that the artificial lipid bilayer membrane is supported on the support layer.

9. The current measuring device as set forth in claim 8, wherein the interval keeping member is made of an elastic material so as to be capable of expanding and contracting.

10. The current measuring device as set forth in claim 8, wherein the support layer is made of polymer gel.

11. The current measuring device as set forth in claim 10, wherein agarose or polyacrylamide is used as the polymer gel.

12. The current measuring device as set forth in claim 11, wherein a thickness of the support layer made of the polymer gel is 50 nm or more and 2 mm or less.

13. The current measuring device as set forth in claim 10, wherein a thickness of the support layer made of the polymer gel is 50 nm or more and 2 mm or less.

14. The current measuring device as set forth in claim 8, wherein a diameter of the membrane formation opening is 10 μm or more and 500 μm or less.

15. The current measuring device as set forth in claim 8, wherein the bottom plate is made of a translucent material, and optical observation means which allows observation of the artificial lipid bilayer membrane on the support layer is provided below the bottom plate.

16. The current measuring device as set forth in claim 8, further comprising: a current measuring means electrically connected to the upper solution chamber; and an earthing means electrically connected to the lower solution chamber.

17. The current measuring device as set forth in claim 8, wherein the artificial lipid bilayer membrane includes an ion channel.

18. The current measuring device as set forth in claim 8, wherein a diameter of the membrane formation opening is more than 20 μm and 500 μm or less.

19. The current measuring device as set forth in claim 8, wherein a diameter of the membrane formation opening is 50 μm or more and 500 μm or less.

* * * * *